United States Patent [19]
Johnston et al.

[11] Patent Number: 5,275,045
[45] Date of Patent: Jan. 4, 1994

[54] APPARATUS AND METHOD FOR USE IN ASSESSING THE LIFTING CAPABILITY OF A HUMAN SUBJECT

[75] Inventors: Joel W. Johnston, Chapel Hill; Edward C. Tibbals, Jr., Jamestown; Gilbert R. Chenery, Raleigh; James E. Miles, Graham, all of N.C.

[73] Assignee: Isotechnologies, Inc., Hillsborough, N.C.

[21] Appl. No.: 665,951

[22] Filed: Mar. 7, 1991

[51] Int. Cl.$^5$ .............................................. G01L 3/24
[52] U.S. Cl. .................................... 73/379.01; 414/21
[58] Field of Search ............... 73/379, 379.01, 379.08, 73/379.09; 364/413.02; 482/38, 91, 110, 901; 901/17, 34; 414/5, 21, 744.3

[56] References Cited

U.S. PATENT DOCUMENTS

| | | | |
|---|---|---|---|
| 3,171,549 | 3/1965 | Orloff | 901/34 |
| 3,752,473 | 8/1973 | LaLanne | 482/38 |
| 3,888,362 | 6/1975 | Fletcher et al. | 901/17 |
| 4,132,318 | 1/1979 | Wang et al. | 901/34 |
| 4,235,437 | 11/1980 | Ruis et al. | 482/5 |
| 4,607,841 | 8/1986 | Gala | 482/91 |
| 4,805,455 | 2/1989 | DelGiorno et al. | 73/379 |
| 4,846,458 | 7/1989 | Potts | 482/26 |
| 4,848,152 | 7/1989 | Pratt, Jr. | 73/379 |
| 4,882,677 | 11/1989 | Curran | 364/413.02 |
| 4,912,638 | 3/1990 | Pratt, Jr. | 364/413.02 |
| 4,969,643 | 11/1990 | Kroeker et al. | 482/112 |
| 4,972,711 | 11/1990 | Jain et al. | 73/379 |
| 5,100,284 | 3/1992 | Boisseau | 414/744.3 |

OTHER PUBLICATIONS

"The LIDO ® Lift," Loredan Biomedical Inc.
"LIFTASK Lifting Capability Screening & Training System," CYBEX division of Lumex Inc.
"Dynatron 2000," Dynatronics.
"TRU-kinetics Work Capacity Torso Testing and Training," Tru-Trac Therapy Products Inc.
"Biolift ® Lifting Analysis and Rehabilitation System," KITS INC.
"Arcon St," Applied Rehabilitation Concepts Inc.

Primary Examiner—Richard E. Chilcot, Jr.
Assistant Examiner—Elizabeth L. Dougherty
Attorney, Agent, or Firm—Richard S. Faust

[57] ABSTRACT

The lifting capacity of a human subject is assessed through dynamic testing protocols utilizing a cylindrical robot that tracks the path of the lift and provides load position information to a data analysis system. The movable linkage of the cylindrical robot moves in a very low friction manner and is designed to be extremely lightweight, while having remarkable strength and rigidity to withstand bending moments and torsional effects. Thus, the apparatus permits three-dimensional lift testing of actual loads, including actual job loads, with the test subject experiencing the true feel and inertial effects of the load. Static force transducers and related means are provided to permit isometric testing.

18 Claims, 16 Drawing Sheets

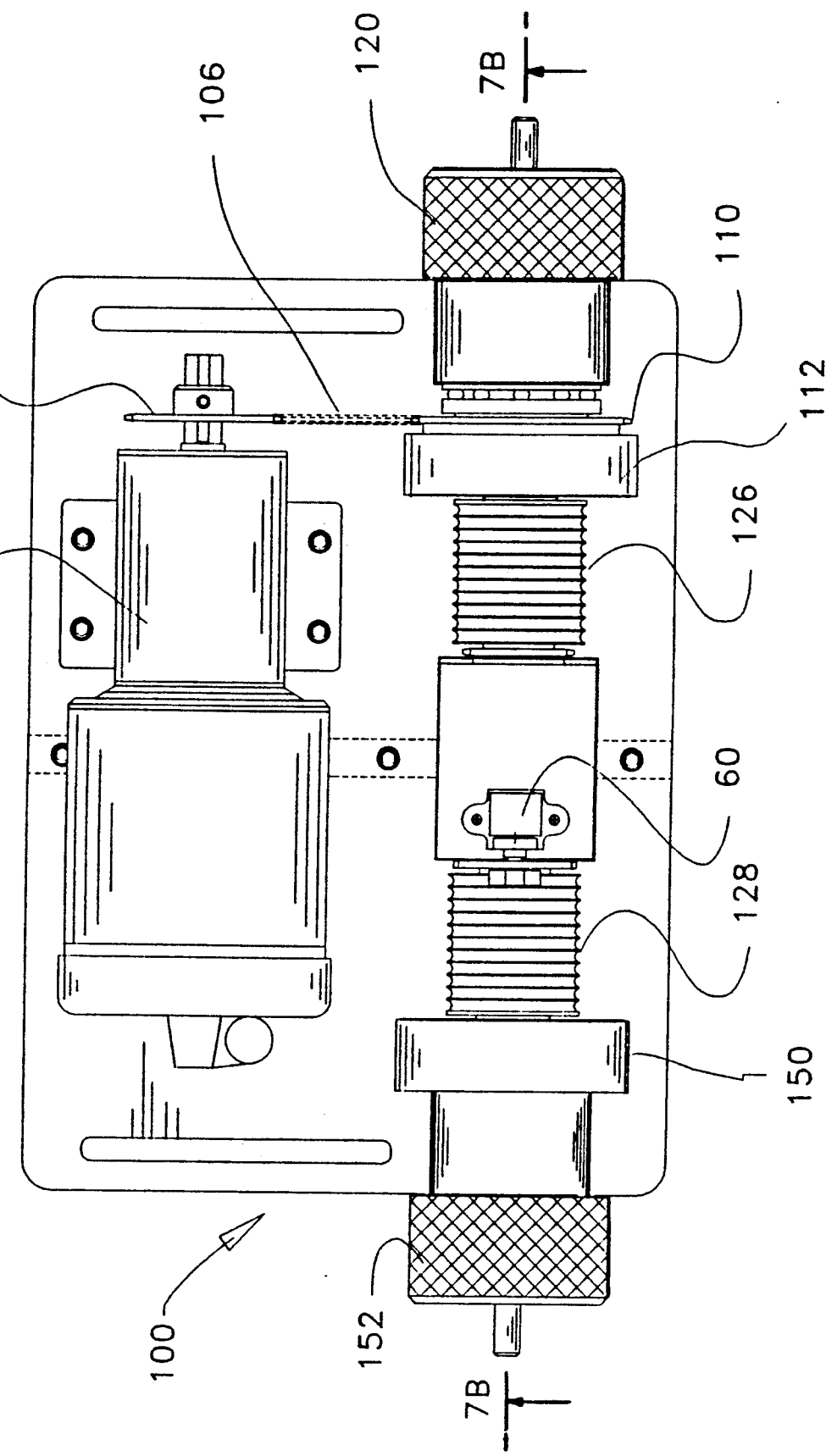

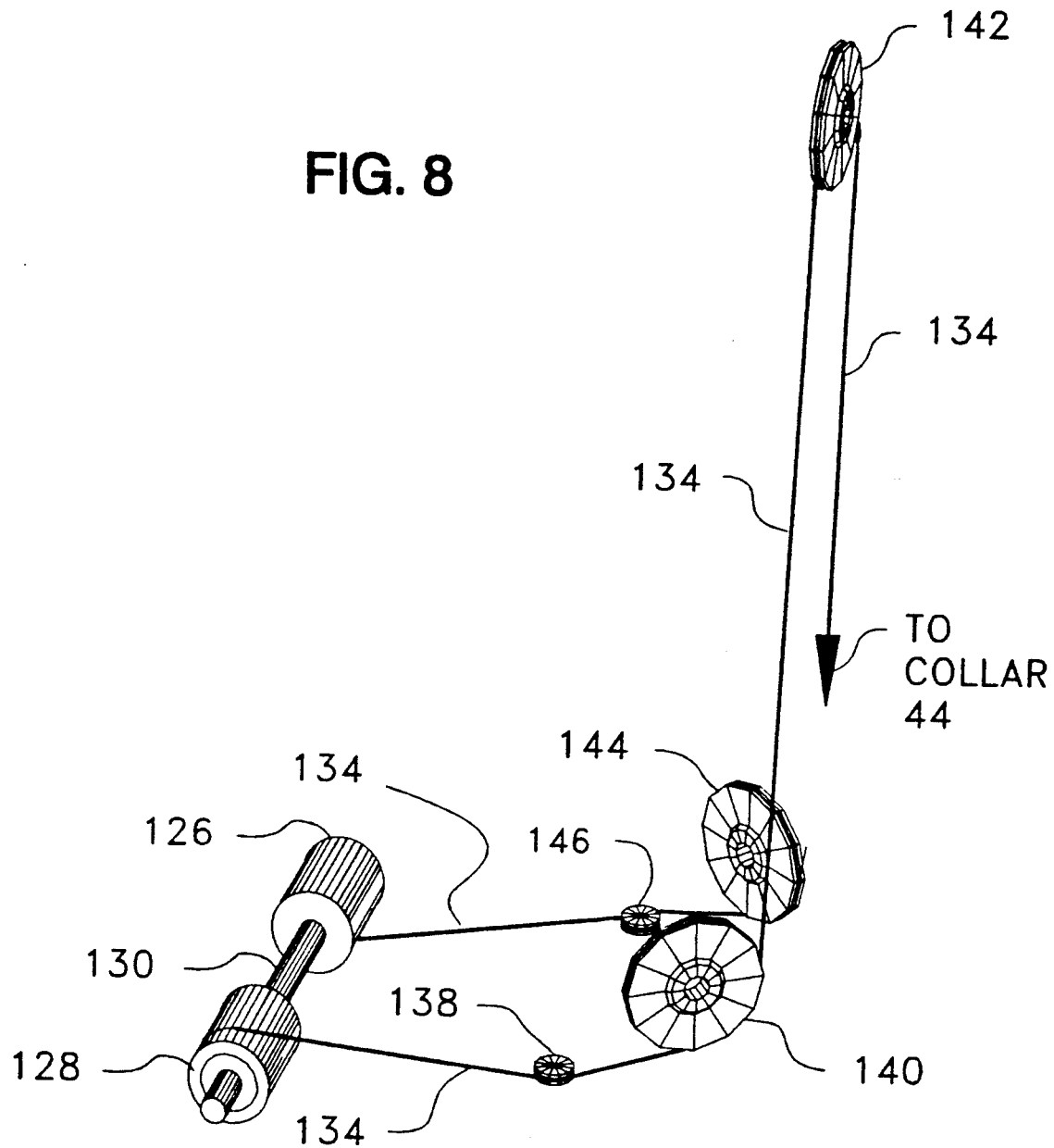

FIG. 9
FIG. 10
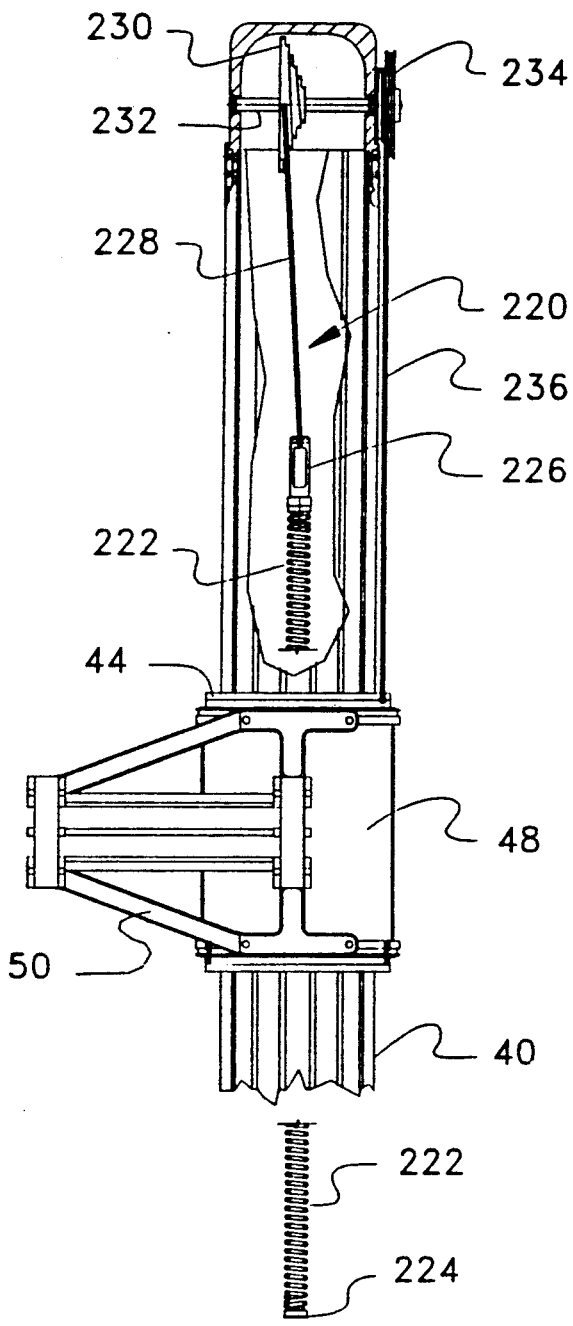
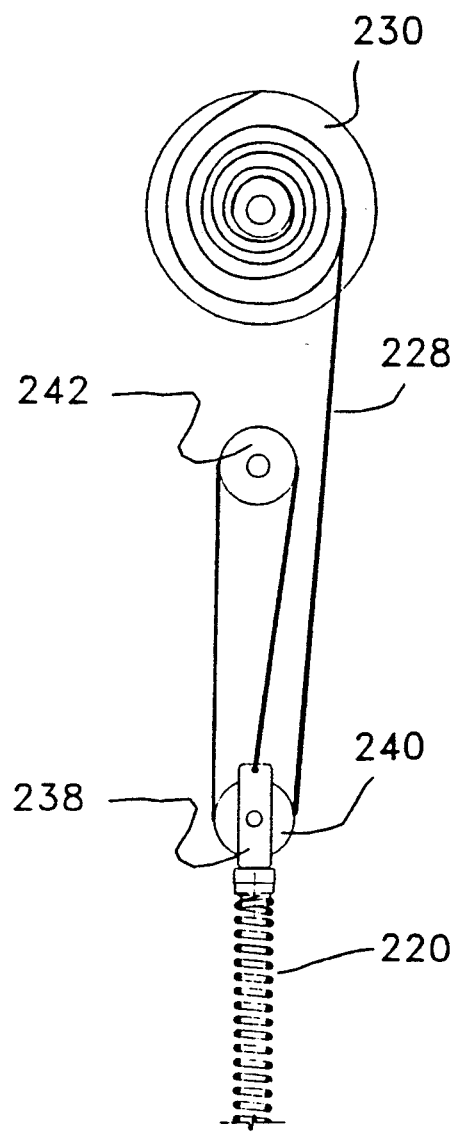

APPARATUS AND METHOD FOR USE IN ASSESSING THE LIFTING CAPABILITY OF A HUMAN SUBJECT

FIELD OF THE INVENTION

The present invention relates to the assessment of human lifting capabilities for the purpose of pre-employment screening, injury verification, or the like.

BACKGROUND OF THE INVENTION

A lifting assessment of an individual is typically performed to determine if the individual can safely perform the tasks required by a job. This assessment can be very specific, or it can be part of a functional capacity evaluation (FCE).

A large amount of research has been conducted to increase the understanding of lifting capacity. The early research utilized static strength testing as the tool for lifting evaluations. The results of this research support the theory that lifting capacity is a function of isometric back strength, and that anthropometric measures are not good predictors of strength. This research, although published in the mid 1970's, continues to be widely recognized in the ergonomics and industrial rehabilitation communities. However, more recent research has shown that dynamic testing is a better predictor of lifting capabilities.

Isometric Lifting

One very specific protocol has been published and is considered the standard procedure for static or isometric testing. See Caldwell et al., "A Proposed Standard Procedure for Static Muscle Strength Testing", *American Industrial Hygiene Association Journal* (July 1974). This protocol consists of a five-second exertion in which a consistent maximal effort is gradually reached in the first two seconds and then held for the remainder of the test. The average force produced during the last three seconds is measured. Since isometric testing is highly postural-dependent, only results from the same body positions can be compared. For this reason, a set of standard static postures appears in the literature.

The National Institute for Occupational Safety and Health (NIOSH) published in 1981 evaluation guidelines entitled "Work Practices Guide for Manual Lifting". These guidelines are widely followed today. The NIOSH guidelines include the results of a study in which the static strength of 1,052 male and 187 female, healthy, industrial workers was measured. This set of data is often incorrectly referred to as the NIOSH norms. The data is not representative of the normal population and, therefore, it should not be used in such a manner. However, the data can be useful in reporting the percentile rankings of an individual relative to healthy industrial workers.

In order to make lifting recommendations for an individual, the lifting frequencies reported must be defined. In general, lifting frequency is divided into three categories: Occasional, Frequent, and Continuous Unfortunately, the literature describes these categories using several different methods. Some of the definitions are based on specifying the number of lifts per minute; some specify the number of lifts per specified number of minutes per specified number of hours, and some specify percentages of the day the lifts are performed (Snook et al., 1970; NIOSH, 1981; D.O.T., 1986). The NIOSH guide uses a very unclear definition that is not regularly followed in functional capacity assessments. The U.S. Department of Labor has published more acceptable percentages in the Dictionary of Occupational Titles, Fourth Edition Supplement (1986). These percentages are defined as follows: Occasional is lifting up to 33% of the day, Frequent is lifting between 34 and 67% of the day, and Continuous is lifting more than 67% of the working day. Given these lifting frequencies, the final step in determining the lifting recommendations from isometric data alone is to make predictions of dynamic strength abilities from static strength measures. As previously mentioned, the early research found isometric back strength to be predictive of lifting capacity. It has been shown that static testing is safe, practical, and reliable, with coefficients of variation (COV) in test-retest scores to be less than 15% (1978).

Dynamic Lifting

Before making extrapolations from the isometric results to dynamic lifting, it is necessary to understand that an isometric test represents only one position of a dynamic activity. For this reason, correlations between static and dynamic activities must be limited to similar postures. It is assumed that the isometric position chosen approximates the maximum lifting requirement of the task, and this is usually the initial phase of a lift. Within the above constraints, the lifting abilities of an individual ca be determined by taking a percentage of the average force produced during the isometric test. The literature reports percentages of 50-75% of the average force for Occasional lifting depending on the posture used during the static test. To determine the Frequent and Continuous lifting recommendations, 40-50% and 20-33% of the Occasional recommendation is calculated, respectively. The percentages used for the Frequent and Continuous calculations are also in agreement with the Strength Factor definitions of the Physical Demand ratings published by the U.S. Department of Labor (D.O.T., 1986).

The research concerning dynamic lifting capabilities focuses on psychophysical, isokinetic and isoinertial lifting. While isometric lifting assessments have shown good correlations with dynamic lifting capabilities, recent research strongly shows that dynamic testing can better determine a person's ability to perform lifting tasks. Static testing does simulate the onset of a dynamic lift when the muscle forces must overcome the inertia of the load, but its main limitation is the inability to account for the dynamic component. Dynamic testing is also less stressful than maximum static exertions.

Many studies have utilized psychophysical lifting as a means to find the maximum capabilities of industrial workers over a given period of time. These studies reveal considerable disagreement about the maximum acceptable weight of lift. Furthermore, the psychophysical method is also very time consuming; it has been found that 40 minutes are required for a person to determine their maximum weight of lift for one task. For these reasons, the psychophysical lifting method is not an acceptable or feasible technique for the dynamic protocol of a lift test machine.

The psychophysical research has revealed other findings that are useful in understanding lifting capabilities. For example, it has been shown that there is a large difference in the maximum acceptable lift in the population. It has also been shown that the lifting capability of a population is at the maximum near the floor level and it decreases as the initial height of the load increases. The size of the box has a significant effect on lifting, with an increase in box size in the sagittal plane accompanying a decrease in lifting ability. Other studies found that the maximum acceptable weights for the combination task of lifting, carrying, and lowering were limited by the lifting and lowering components. Finally, it has been found that there is no significant difference in the maximum acceptable weights between lowering and lifting tasks.

In 1978, S. Snook combined the results of seven studies following the psychophysical lifting protocol and created tables based on object width, vertical distance of lift, and frequency of lift. In 1990 the results of four recent psychophysical studies were compiled with the data published in 1978 to produce revised tables that can be useful in estimating dynamic lifting capabilities in industrial settings.

While the dynamic component of a lift can be better accounted for in isokinetic testing than in isometric testing, isokinetic activities, nevertheless, have limitations in simulating actual dynamic tasks.

In 1986 Jiang et al. recommended isoinertial testing as the most promising single screening test because it more closely simulated lifting tasks by involving both the static and dynamic components. The Jiang study utilized an incremental weight-stack device to create an isoinertial lift. The device allowed the subjects to increase psychophysically the weight in 2.5 pound increments to determine the maximum they were able to lift. This is a variation of the traditional psychophysical method and it requires far less time. It was found that the isoinertial strength could be determined in 5 to 10 repetitions. The results of this study found a floor-to-overhead lift to be highly correlated with lifting capacities ($r=0.85$ to $0.95$). The limitation of this study is a safety concern for the individual. If the weight is too heavy to be lifted and the person drops the handles, both the individual and the device are at risk of impairment.

Once the maximum lifting ability is measured for an individual, the next concern is determining whether the load can be handled safely. Lifting activities are unsafe when excessive stress is placed on the trunk. The back muscles cannot overcome the resultant compressive forces experienced by the spine during excessive loading. The forces acting on the spine, combined with the overuse of muscles, can lead to low back injury.

NIOSH (1981) published limits that provide assistance in determining whether a lift causes unacceptable compressive forces to be generated. These limits are based on the weight of the load, the initial position of the load relative to the person, the vertical travel distance between the origin and the destination, and the frequency of the task. The Maximum Permissible Limit (MPL) is the point at which most workers cannot tolerate the compressive forces on the 1.5/S1 disc. Only 25% of men and less than 1% of women have the muscle strengths capable of performing work above the MPL. The Action Limit (AL) is based on disc compression forces that can be tolerated by most young, healthy workers. Over 99% of men and 75% of women can lift loads defined by the AL. NIOSH states that tasks over the MPL are unacceptable, and tasks between the MPL and the AL are unacceptable without job screening or redesigning. Tasks below the AL present the least amount of risk to workers.

The research on dynamic lifting has investigated the types of tasks commonly performed in manual materials handling (MMH). In 1970, Snook et al. divided MMH into six basic tasks: lifting, lowering, pushing, pulling, carrying, and walking. Snook claims that almost every MMH task in industry consists of a combination of two or more of these tasks. Other studies support this claim.

In 1982 Drury et al observed over 2000 different box-handling tasks performed in industrial settings and found the three most common tasks to be lifting, lowering, and carrying. This study found that sagittal, symmetrical lifting tasks are the exception rather than the rule, and that many lifts involve body twisting as boxes are handled. Of the 2000-plus lifts, over 90% were two-handed in nature, but only 2.6% of the tasks used boxes with handles. The most common lift began with the box away from the body at a height between 12 and 60 inches. The lift was initiated with the body rotated to the right (20 to 40% of the time), and there was virtually no twisting during the carry phase, with a median carry distance of five feet. The task was completed with a twist to the left as the box was lowered (40 to 75% of the time).

A 1982 survey compiled by the U.S. Department of Labor, with over 900 blue-collar workers responding, investigated the nature of back injuries associated with manual materials handling. Seventy-seven percent of the injuries occurred during activities that featured lifting, versus placing, carrying, lowering, holding, pushing, and pulling activities. Over half of the injuries occurred when the worker was bending (56%) and one-third involved twisting or turning. In 46 percent of the cases, the arms were extended down, the back was slightly bent (58%), and the legs were slightly bent (55%). Before the lift was initiated, the object was on the floor in 52 percent of the cases, and the object was placed either at waist height (23%) or on the floor (17%). In 47 percent of the injuries, the worker did not carry the object any distance, while 28 percent of the workers carried it less than five feet. When the object was held or carried, 66 percent of the workers held or carried it for less than one minute. Thirty-six percent of the injuries occurred because the object was too heavy; 34 percent of the injuries were the result of a body movement or motion, and 24 percent were the result of the object being too bulky. This survey indicates that most injuries occur when objects are lifted between floor level and waist height as a person is either bending or twisting and turning.

The literature clearly points out a need to simulate a job task closely during testing in order to improve predicting the maximal lifting capabilities. Recent studies have demonstrated the importance of including the naturally occurring asymmetric and functional components of a lift into lifting assessment procedures. Also, the introduction of the Americans with Disabilities Act in 1990 shows the significance of improving the job selection process by requiring all screening tests to the essential tasks being investigated or tested.

Devices currently available for lifting evaluation include, among others, the Dynatron 2000, Cybex Lift-Task, True-Kinetics and Biolift machines. These machines use various combinations of isometric and push-pull protocols to provide weight recommendations for the test subject expressed as different frequencies of lifting over a period of a day. However, none of these machines permits three-dimensional lifting tests that simulate or recreate the naturally occurring asymmetric, acceleration and inertial components of a lift.

In the field of exercise and rehabilitation machines, U.S. Pat. No. 4,235,437 to Ruis et al. discloses a machine that represents a dramatic departure from traditional machines. This machine provides a rigid frame and a linkage of multiple links. A user interaction point is attached to one of the links and permits the user to move the interaction point to any desired position within a two-dimensional plane or three-dimensional region. Position sensors operate in response to the user's movement of the device to provide location signals that are indicative of the actual position of the links and user interaction point. Through a feedback control system and servo motors, the machine has the capability of being programmed to provide a desired path of exercise motion which controls the forces or torques supplied to each link in order to constrain the path of exercise motion to the desired path.

The recent introduction of the LIDO lift machine provides a machine that includes a cylindrical robot structure and an associated close loop feedback control servo mechanism that actively controls the cylindrical robot to simulate gravity and inertial effects in lifting tests.

The subject's interface with this machine is, therefore, not with an actual load, but with a user interface that attempts to simulate, but does not recreate, the true asymmetric, acceleration and inertial components of a lift. This machine operates in a gravity-inertia mode, an isokinetic mode and an isometric mode.

While extensive academic research has indicated the need for a lift capability testing apparatus that includes dynamic modes of operation capable of faithfully recreating three-dimensional lifting tasks encountered in actual manual material handling jobs, to date no machine truly accomplishes that purpose.

SUMMARY OF THE INVENTION

The present invention provides a novel and versatile apparatus that permits both isometric and dynamic testing of human subjects to assess their lifting capabilities. The machine is operative in an isometric mode wherein the movable linkage of the apparatus is locked into a static structure permitting the subject to perform standard push-pull, lifting and other isometric tests. In the dynamic mode of operation, the apparatus may be used with standard loads, e.g. weights in a box, or in the alternative, may be used with actual job task loads, e.g. boxes, bags, asymmetrical loads, or the like.

The apparatus is designed so that in the dynamic mode the test subject experiences the "true" inertial effects of the actual loads that he lifts, resulting in a "feel" that is lifelike and faithfully recreates the experience of an actual three-dimensional lifting task. Stated differently, one goal of the present invention is to make the apparatus "invisible" to the test subject so that the test results are not tainted by apparatus induced resistance, inertia or the like.

The realistic, lifelike lifting experience created by the apparatus of the present invention is achieved by an apparatus that includes a movable linkage which defines an endpoint having three-dimensional freedom of movement. The device includes means for attaching an actual load proximate the end point of the linkage and permitting the test subject to manually engage the load in a realistic fashion. The device further includes means for sensing relative movements within the linkage during lifting of the actual load and generating signals representative of the position of the endpoint. The device is operated in an essentially passive mode during dynamic lifting operations performed by the subject.

In a preferred embodiment, the movable linkage is part of a so-called cylindrical robot that includes an upright column and a horizontal arm mounted for vertical movement along the column, rotatable movement about the column and linear extension and retraction. In this embodiment, the low inertial effects and "true" feel are achieved in large part by the provision of low friction bearings at the points of movement within the linkage, while the mass of the arm and related movable elements is held to a minimum. Despite their low mass, the movable members must, nevertheless, withstand the forces and torques created by actual loads in three-dimensional lift testing. These members, must also remain rigid in all directions during the exertion of significant force by the test subject in isometric testing.

The low inertial effects experienced during lifting are also achieved by the provision of a counterbalancing mechanism that counterbalances the weight of the moving members during lifting operations.

The apparatus preferably includes a drive assembly useful for raising or lowering the arm member and attached load prior to or after a test procedure. The drive assembly can also serve to lock the arm against vertical movement when is desired to place the apparatus into an isometric testing mode. Finally, the drive assembly may be controlled by the system computer to provide a safety brake function for engaging and locking the arm and attached load against dropping upon sensing the test subject's loss of control of the load.

Various means may be used for attaching the actual loads to the endpoint of the arm. In a preferred embodiment, a universal attachment means is used to attach actual job loads such as bags, boxes, asymmetrical loads or the like. For use in isometric testing, the dynamic load attachment means may be removed and replaced with a pair of spaced apart handles.

The system software is a protocol-driven lifting evaluation software package, designed to implement multiple protocols. The software produces reports for each testing protocol and testing screens that guide the user through each test. Two simple protocols are able to demonstrate the capabilities of the software, provide a means to test individuals, create a database of those individuals tested, and allow comparison of an individual to groups of individuals in a database. The protocols assess an individual's lifting capabilities, yet operate simply. The software is designed with the flexibility necessary to add protocols as particular users' needs arise.

The Comprehensive protocol includes both isometric and dynamic tests, while the Isometric protocol consists only of isometric tests. The Isometric protocol allows the user to conduct a complete assessment, with up to seven different static positions, based on standards from the literature. The Comprehensive protocol consists of a subset of the isometric tests, a set of standard dynamic tests, both two-dimensional (2D) and three-dimensional (3D), and a job task simulation phase.

DESCRIPTION OF THE DRAWINGS

Some of the objects having been stated, other objects will appear as the description proceeds, when taken in connection with the accompanying drawings, in which

FIG. 7A is an enlarged, detailed top view of portions of the drive assembly.

FIG. 8 is a schematic representation of the path of the recirculating cable of the drive assembly.

FIG. 9 is a side view of portions of the cylindrical robot with portions cut away to show the counterbalance system.

FIG. 10 is side view showing an alternative counterbalance system.

DETAILED DESCRIPTION OF THE INVENTION

While the present invention will be described more full hereinafter with reference to the accompanying drawings, in which aspects of the preferred manner of practicing the present invention are shown, it is to be understood at the outset of the description which follows that persons of skill in the appropriate arts may modify the invention herein described while still achieving the favorable results of this invention. Accordingly, the description which follows is to be understood as being a broad, teaching disclosure directed to persons of skill in the appropriate arts, and not as limiting upon the present invention.

Figure 1:
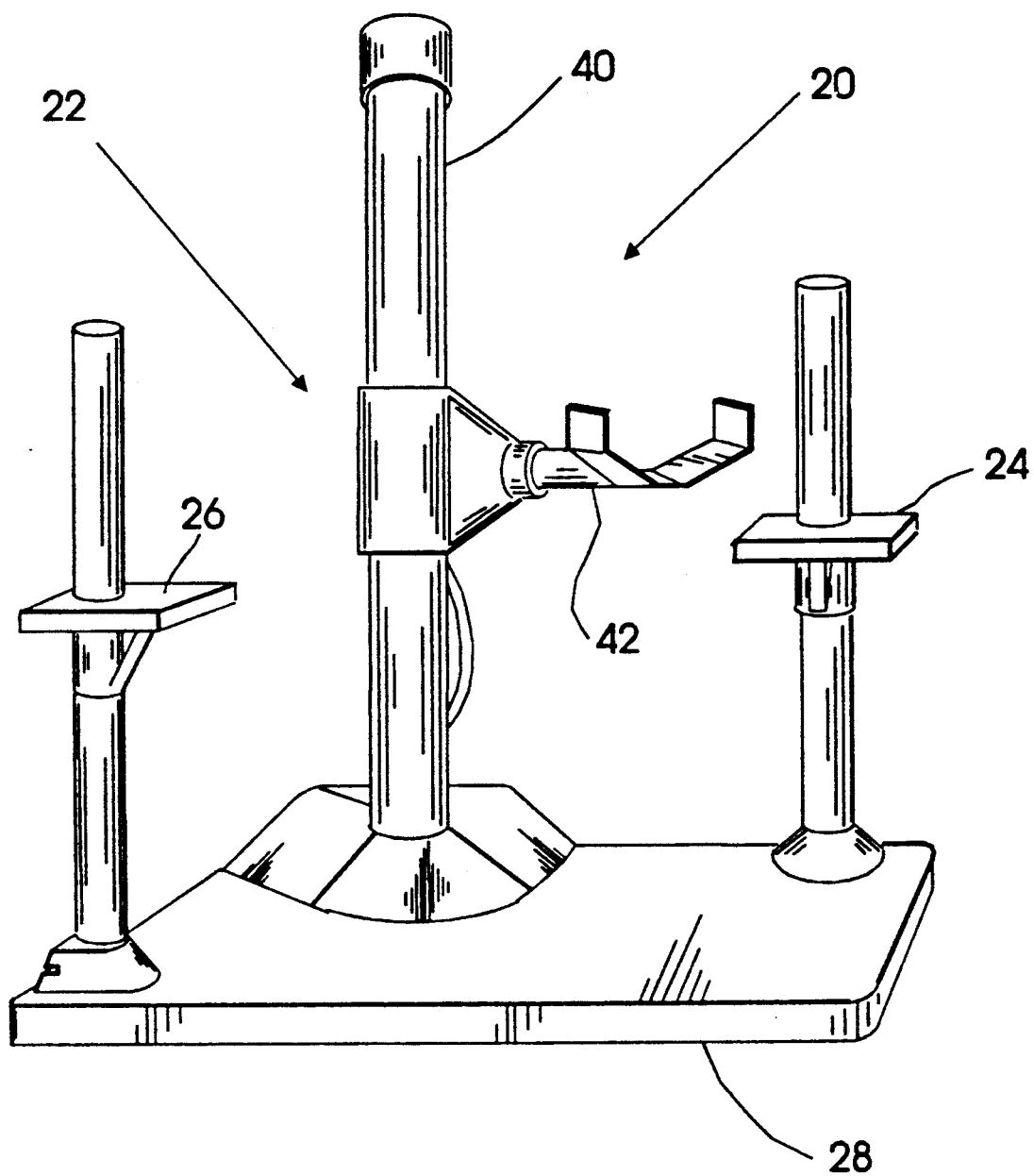
FIG. 1 is a pictorial representation of a lifting capability assessment apparatus of the present invention.

Referring to the drawings, and particularly to FIG. 1, there is shown a lifting capability assessment apparatus 20 constructed in accordance with the present invention. Apparatus 20 includes a cylindrical robot 22, a first adjustable shelf 24, a second adjustable shelf 26 and a platform 28. During lifting operations, platform 28 serves to provide a closed force system. A computer (not shown in FIG. 1) is provided for data acquisition and analysis in the manner described in detail below.

Cylindrical robot 22 is the preferred form of apparatus for providing the movable linkage necessary to create the three-dimensional freedom of movement required in lifting operations. The movable linkage includes multiple "links". The term "link" is used in this description and in the claims in its kinematic sense, meaning a structure or body of arbitrary shape and construction which is sufficiently rigid to maintain its shape and which is a member of a movable linkage, or group of links. In a dynamic mode of operation this linkage interacts with the user by means of one of various load attachment means, discussed below, which is located on the outermost link of the linkage. The area of load attachment and user interaction will be referred to as the "endpoint".

There are several alternative ways to construct the linkage within the context of this invention. Links may be joined together by hinge joints allowing one link to rotate relative to another. They may be joined together by a guideway allowing one link to move in a straight line relative to another. Different pairs of links within a linkage may be joined in either of the above ways.

Cylindrical robot 22 comprises an upright column 40 which is fixedly secured at its base to platform 28 and extends upwardly to a height sufficient to accomodate a full range of lift task operations, for example, to a height of approximately eight feet. The outer link of the cylindrical robot is a horizontal arm 42 which is free to move vertically on column 40, rotationally about the axis of column 40 and in linear extension and retraction. The outer end of arm 42 defines the "endpoint" of the movable linkage. The endpoint is movable in a three-dimensional region as described below.

Figure 4:
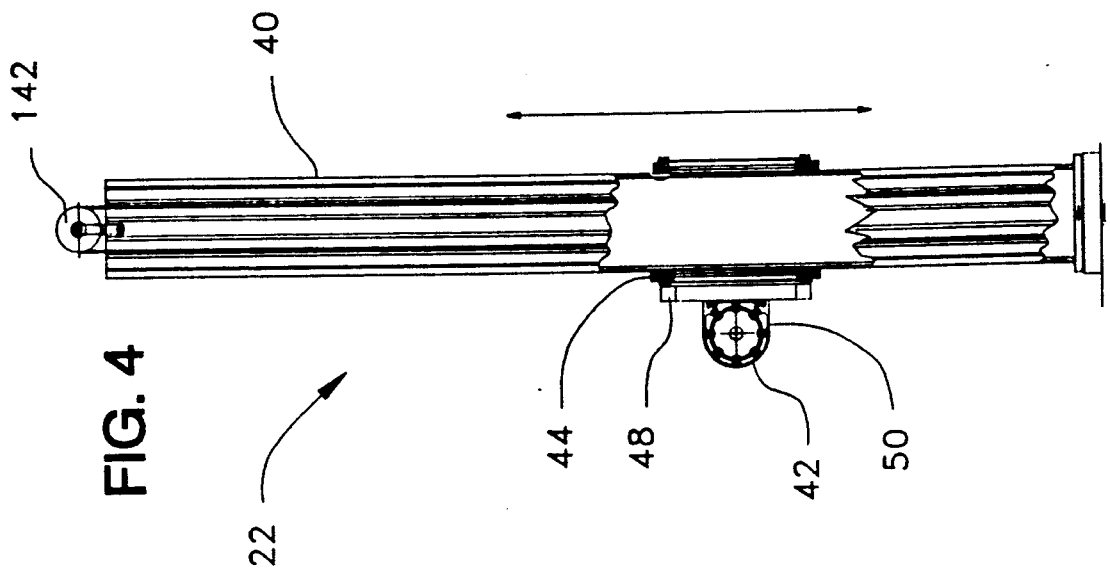
FIG. 4 is another view of the cylindrical robot as seen in the direction of arrow 4 of FIG. 3.
Figure 3:
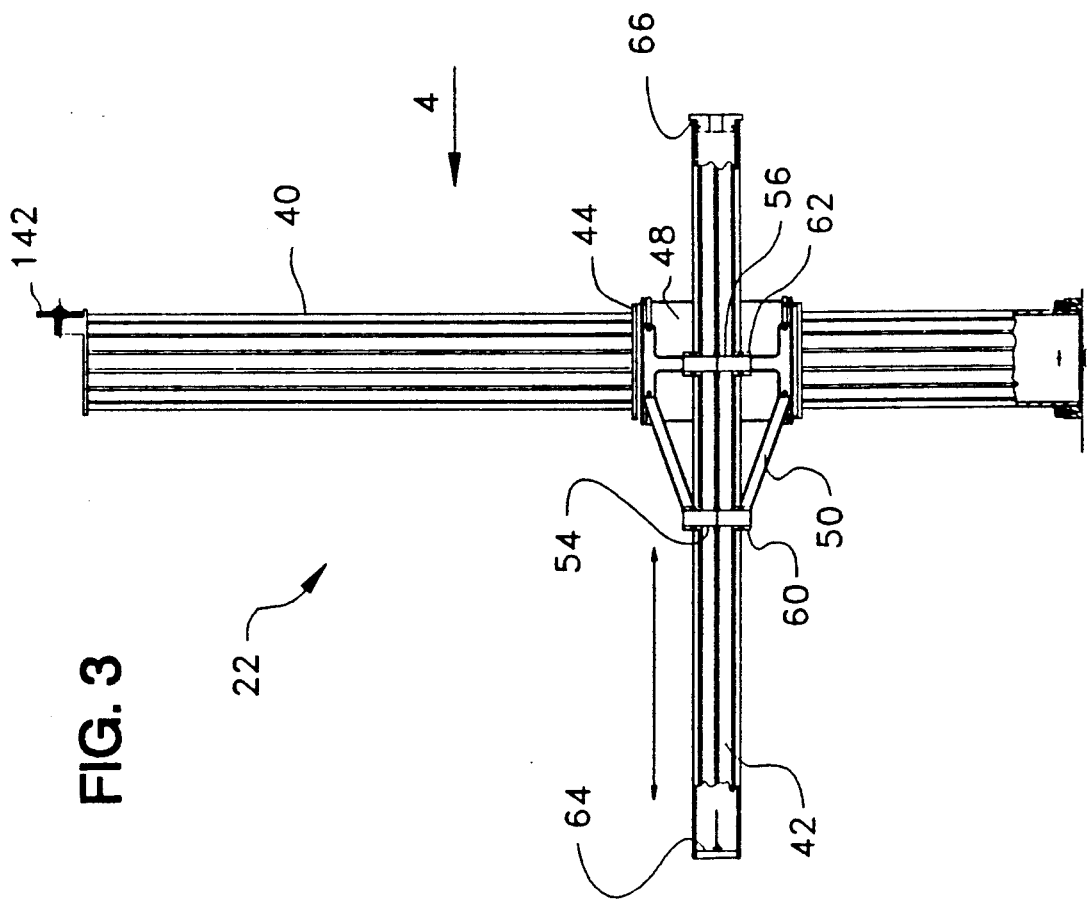
FIG. 3 is a side view of the cylindrical robot type of linkage incorporated into the apparatus of FIGS. 1 and 2.
Figure 5:
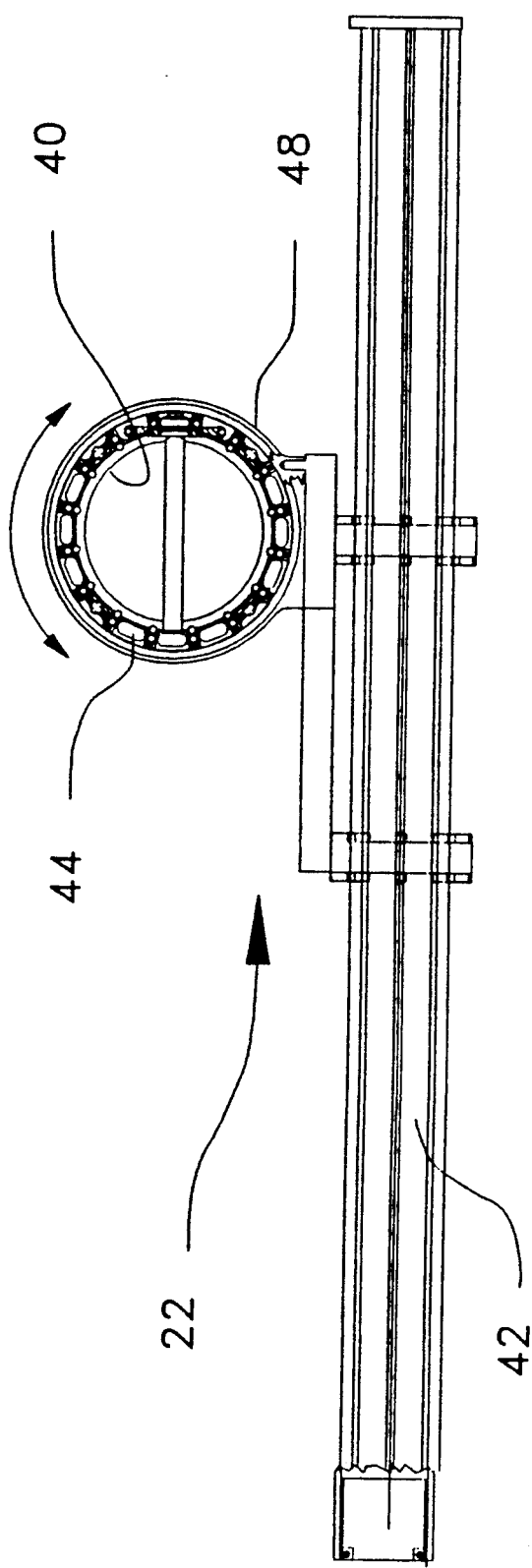
FIG. 5 is a top view of the cylindrical robot illustrated in FIGS. 3 and 4.

The complete movable linkage of cylindrical robot 22 will now be generally described with reference to FIGS. 3-5, with a detailed discussion of the low friction bearings being presented immediately below in connection with FIG. 6. The first link of the movable linkage is a collar 44 that is mounted for low friction vertical movement along the outer surface of column 40. A cylindrical carriage 48 that is concentric with collar 44 is rotatably mounted over the collar and has rotational freedom about the collar. A frame assembly 50, substantially in the form of a sideways "A", is fixedly secured to the rotatable carriage 48. Frame assembly 50 includes a pair of openings 54, 56 that slideably receive the above mentioned arm 42 for linear extension and retraction. Stops are provided at 60 and 62 (FIG. 3) to engage mating stop members 64, 66 carried at the ends of arm 42 to limit the linear movement between a fully retracted position where stop 60 engages stop member 64 to a fully extended position where stop 62 engages stop member 66, a linear travel of approximately 32 inches.

The low friction bearing assemblies that facilitate the movement of the above linkage of the cylindrical robot will now be described with primary reference to FIG. 6. Referring first to the vertical movement component, the cylindrical outer surface of column 40 includes a series of vertically extending ball races 70 that receive recirculating linear bearings 72 that are housed within the vertically movable collar 44 (see broken away portion of FIG. 6).

Figure 6:
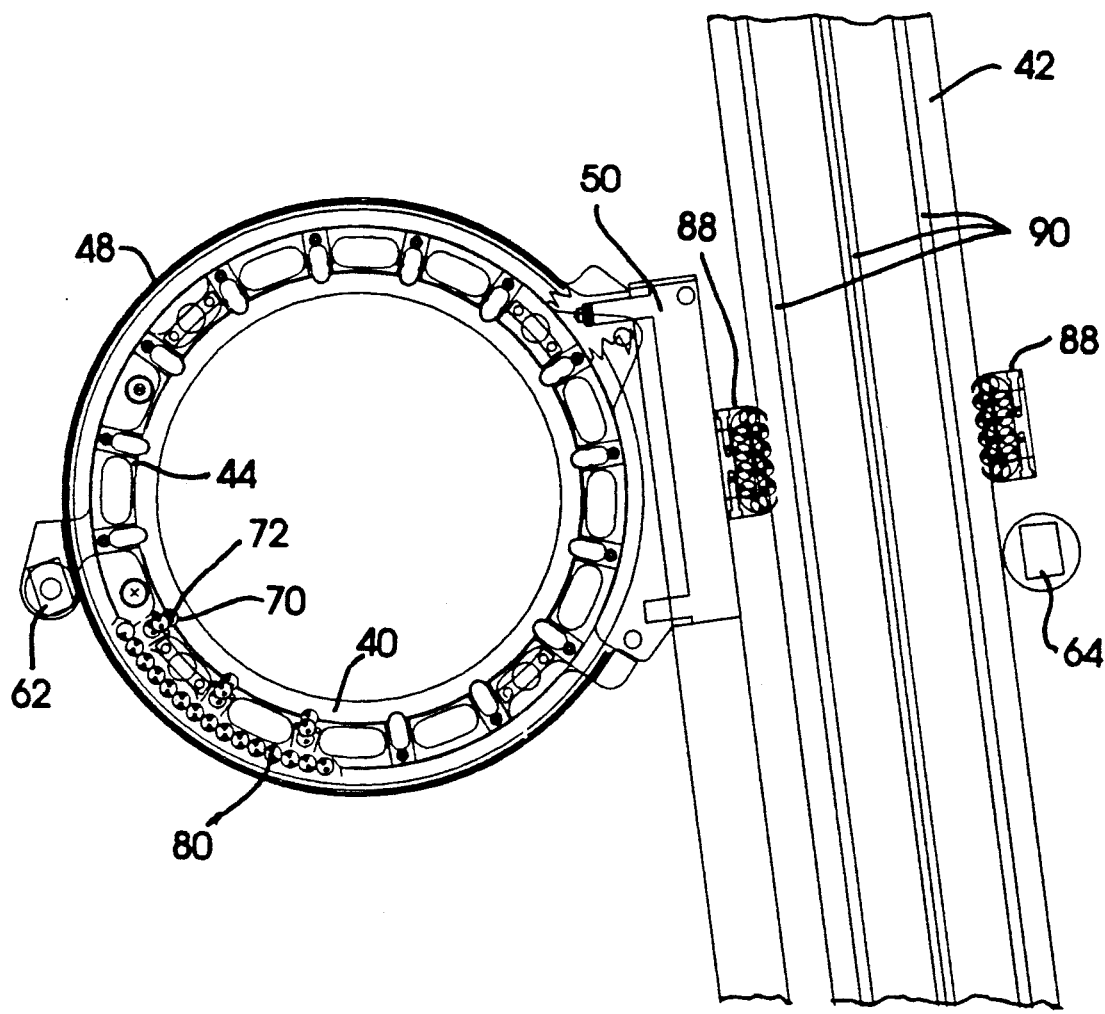
FIG. 6 is an enlarged top view, partly broken away, showing the bearings permitting low friction vertical and rotational movement and extension/retraction of the arm.

FIG. 6 also illustrates one of the two low friction ball bearing assemblies that permits concentric carriage 48 to rotate about collar 44. One such bearing assembly is located at the top of carriage 48 and another at the bottom thereof. The ball bearing assembly includes ball bearings 80 and cooperative circumferential grooves (not shown in detail) in carriage 48 and collar 44.

FIG. 6 also illustrates in a somewhat schematic fashion the relationship between arm 42 and two of the recirculating linear bearings 88 that are mounted within the openings 54 and 56 of frame assembly 50 and facilitate the low friction linear movement of arm 42. The bearings of assemblies 88 travel in linear races 90 located on the outer surface of arm 42.

In a preferred embodiment, column 40 and arm 42 are formed as tubular members of aluminum. The surfaces for all rolling contacts with the mentioned recirculated linear bearings are Teflon impregnated, hard anodized aluminum which provides a hardened, wear resistant surface (harder than heat treated steel) and a dry lubricating effect achieved by the Teflon impregnation.

The above-described bearing assemblies have been specifically chosen to provide low friction movement between the movable links of the cylindrical robot to enhance the realistic "feel" of lifts performed with apparatus 20. Furthermore, the materials and structural design of these elements have been chosen to minimize the mass of the movable linkage while at the same time maintaining rigidity during both dynamic operations and the substantial bending moments and torsional effects caused by isometric operations.

Figure 2:
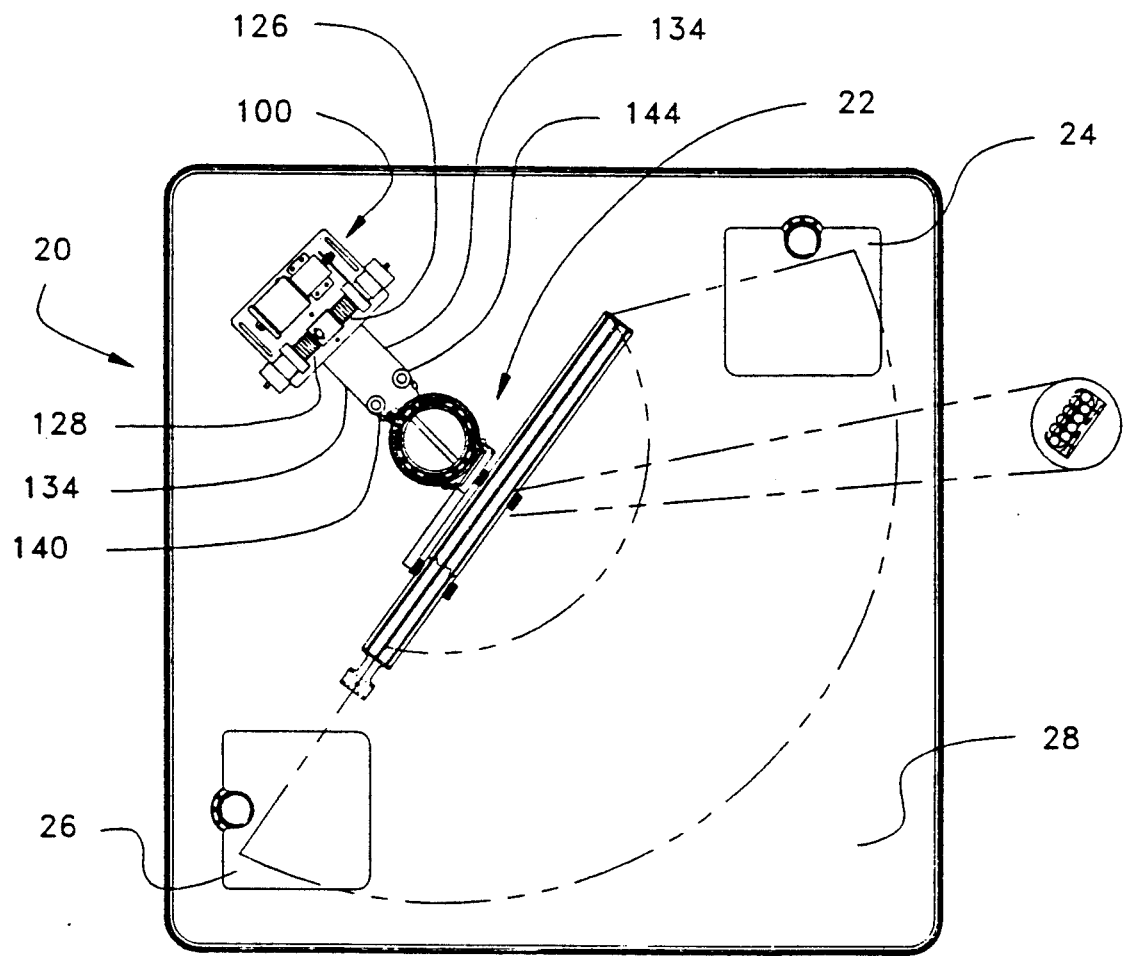
FIG. 2 is a top view of the apparatus illustrated in FIG. 1 showing the arcuate three-dimensional region of movement of the endpoint and load.

It will be appreciated that cylindrical robot 22 provides a linkage including three links. The outermost link, arm 42, defines an endpoint that is movable within a three-dimensional arcuate region as best shown in FIG. 2. In the illustrated embodiment, the arcuate region defines an arc on the order of 140 degrees, a width measured from the inside arcuate boundary to the outside arcuate boundary of approximately 32 inches, and a height that is somewhat less than that of column 40, e.g., approximately 63 inches.

With respect to the above definition of a linkage and its constituent links, cylindrical robot 22 provides a first guideway link defined by the vertical displacement of collar 44 along column 40. Robot 22 also defines a second rotational link defined by the rotation of carriage 48 and frame assembly 50 about the vertical axis of column 40. The third link is defined by the guideway movement provided by the linear movement of arm 42 with respect to frame assembly 50.

Other structures, for example an elbow arm structure or a gantry structure, may be utilized to provide the necessary linkage.

A position sensor is provided for each link to sense the relative movement of that link with respect to another link during lifting operations. In this regard, position sensor 60 senses vertical movement of collar 44 with respect to column 40 by measuring cable movement in the drive assembly, as discussed in detail below in connection with FIGS. 7A and 7B. A second position sensor 62 (FIG. 6) senses the rotational movement of carriage 48 and frame assembly 50 with respect to collar 44. The third position sensor 64 (FIG. 6) measures the linear displacement of arm 42 with respect to frame assembly 50. Each position sensor 60, 62, 64 generates signals indicative of the position of one link with respect to another link in the linkage with the signals together being representative of the position of the endpoint.

For use of apparatus 20 in two-dimensional dynamic testing, one-dimensional dynamic testing (i.e. linear or curvilinear) or static isometric testing, cylindrical robot 22 is provided with means for selectively locking a selected number of links against movement with respect to the other links. The locking function may be achieved by manually operative means such as locking pins or by computer controlled locking mechanisms. In a preferred embodiment, locking pins (not shown) are utilized to lock arm 42 with respect to frame assembly 50 and to lock carriage 48 against rotation with respect to column 44. The locking of vertical movement of collar 44 with respect to column 40 is achieved through the drive system as described below.

The description will now turn to a discussion of the drive assembly 100 which serves as a computer controlled drive system for driving collar 44 and the attached linkage vertically along column 40 when it is desired to move the actual load to the starting point of the test operation or, in other instances, were it is desired to position the "endpoint" near floor level for attachment of an actual load.

Figure 7B:
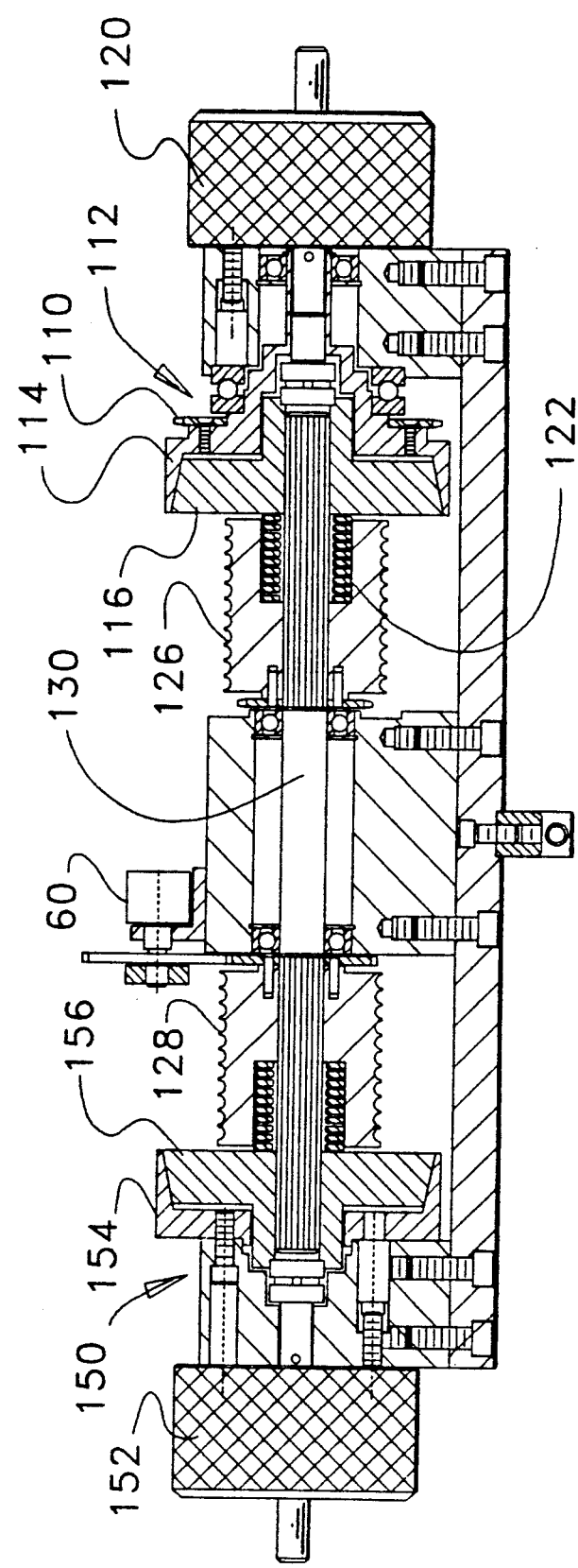
FIG. 7B is a section view of portions of the drive assembly taken substantially along line 7B—7B of FIG. 7A.

As illustrated in FIG. 2, the principal components of drive assembly 100 are located on platform 28 at a location that will not interfere with movement within the arcuate testing region. With further reference to FIGS. 7A and 7B, drive assembly 100 includes a directional gear motor 104 which drives a chain 106 by means of a motor sprocket 108. Chain 106 in turn engages the clutch sprocket 110 of a spring actuated drive clutch 112. Sprocket 110 is fixedly secured to a clutch driver 114 which is engaged or disengaged with respect to a drive cone 116 according to the directional status of a drive solenoid 120. When not energized, by computer command, solenoid 120 serves to engage driver 114 and drive cone 116 against the bias of a compression spring 122 to permit directional motor 104 to drive the paired cable spools 126, 128 carried on spool shaft 130. A cable 134 (FIGS. 2 and 8) connected to collar 44 is reeled out and taken up on spools 126, 128 to either raise or lower collar 44 and the associated linkage and load according to the direction of drive of motor 104.

Cable 134 is shown in the top view of FIG. 2 as it travels from spools 126, 128 to the guide pulley arrangement leading to collar 44. The schematic diagram of FIG. 8 shows that the recirculating cable is directed by a series of guide pulleys 138, 140, 142 (at the top of column 40), 144 and 146. The end of cable 134 is affixed to collar 44.

The drive assembly also includes a brake clutch 150 that is similar in construction to the above mentioned drive clutch 112. Brake clutch 150 includes a brake solenoid 152 which operates through driver 154 and drive cone 156 to lock spool shaft 130 against rotation when it is desired to lock the vertical orientation of the linkage and attached load, for example, during isometric testing. Brake clutch 150 also serves as a safety brake mechanism which, as explained below, operates to lock the linkage and load against falling when the system senses that the test subject has lost control of the load.

The counterbalance assembly 220 will now be described with reference to FIGS. 9 and 10. Assembly 220 includes a tension spring 222 that is secured at its lower end 224 to the base of column 40. Spring 222 extends upwardly to a point of securement to a member 226 that attaches the spring to a cam cable 228. Cable 228 then attaches to a grooved spiral cam 230 which converts the variable linear force exerted by spring 222 into a constant input torque to shaft 232. Shaft 232 conveys the contact torque rotary motion to counterbalance takeup spool 234 which converts the constant torque to a linear constant force via cable 236. The constant force conveyed by cable 236 is applied to collar 44 via cable attachment. The selection of an appropriate spring constant for spring 222 in combination with the appropriate grooved spiral arrangement for cam 230 produces a constant force substantially equal to the weight of collar 44 and attached linkage assembly to counterbalance the effects of gravity, i.e., the weight of collar 44 and attached linkage.

FIG. 10 depicts an alternative pulley arrangement for connecting spring 220 to cam 230 via cable 228. This arrangement includes a pair of idler pulleys 240, 242 that create a triple lead path for the cable for the purpose of permitting the use of a smaller takeup pulley at 234.

Figure 11:
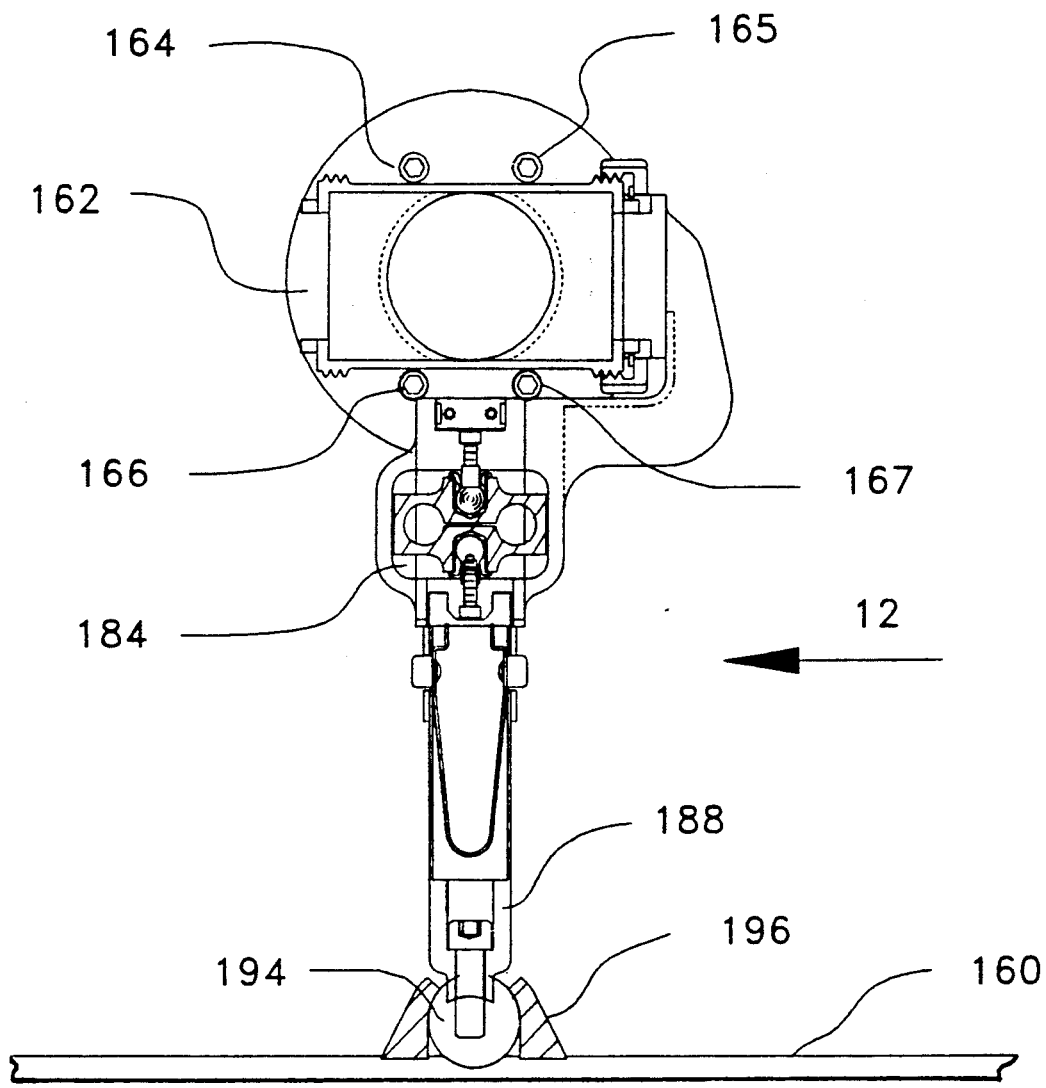
FIG. 11 is an end view of the universal load attachment means as utilized to attach a wide variety of actual job loads, e.g., boxes, bags, asymmetric loads, or the like, proximate the endpoint of the arm.
Figure 12:
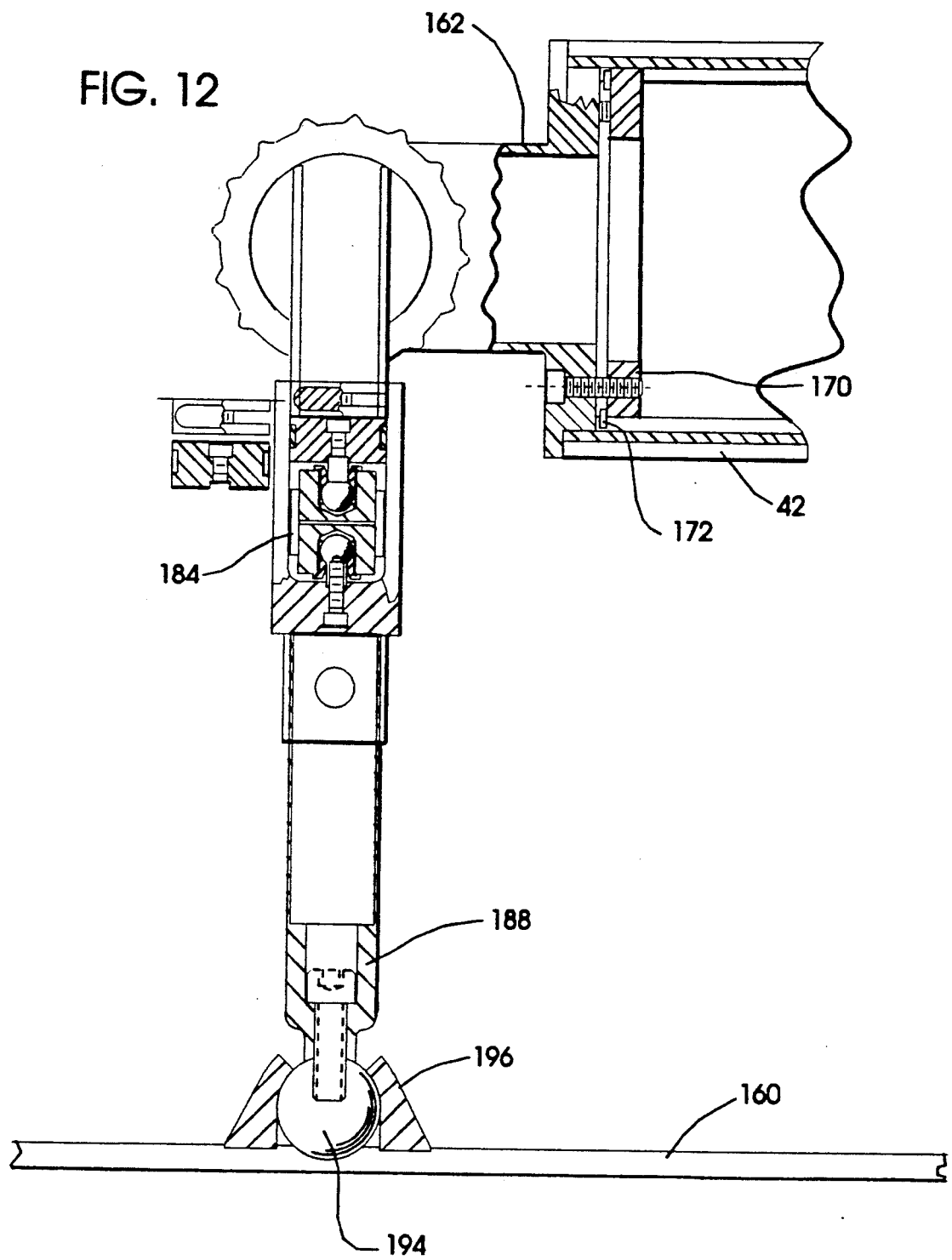
FIG. 12 is a side view of the universal load attachment means as seen in the direction of arrow 12 of FIG. 11.
Figure 13:
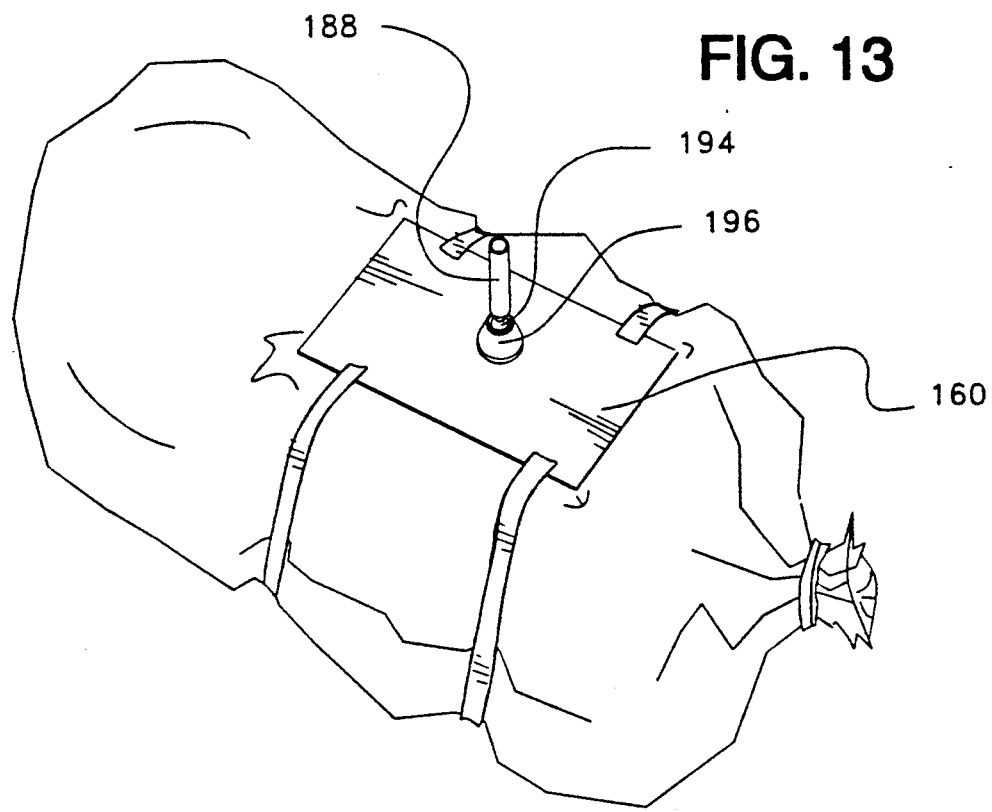
FIG. 13 is a view of an actual job task load attached to the arm.

Referring to FIGS. 11-13, there is shown a universal load attachment means for securing an actual load to the endpoint of arm 42. In the illustrated embodiment, the load attachment means takes the form of a depending arm structure that connects the end of arm 42 to a universal load securement plate 160. Plate 160 may be used with associated belts, bands, or the like, to secure an actual load.

The depending arm structure includes a trunion 162 that is secured to the end of arm 42 by means of four bolts 164, 165, 166, 167 that connect the trunion to an internal retaining collar 170 through a snap ring spacer 172. Trunion 162 includes a plurality of ribs that are received in mating slots in the retaining collar to achieve a secure mating of the trunion to arm 42 and to spread the torsional loads and bending moments from both dynamic and isometric tests uniformally over the entire circumference of arm 42. This type of load distribution is important in this area of the structure due to the substantial loads being transmitted versus the limited mass of arm 42 and related components, all of which, as explained above, are formed to be as light in weight as possible to reduce the inertial effects of the linkage during testing operations.

Trunion 162 connects to a depending structural member which carries a load cell 184 for sending signals to the computer representative of the weight of the load. By means of a connector 188, the load cell is connected to a ball 194 that is received in a socket 196 secured to plate 160.

FIG. 13 illustrates the attachment of an actual job load to arm 42 by means of an attachment means similar to that illustrated in FIGS. 11 and 12.

Figure 15:
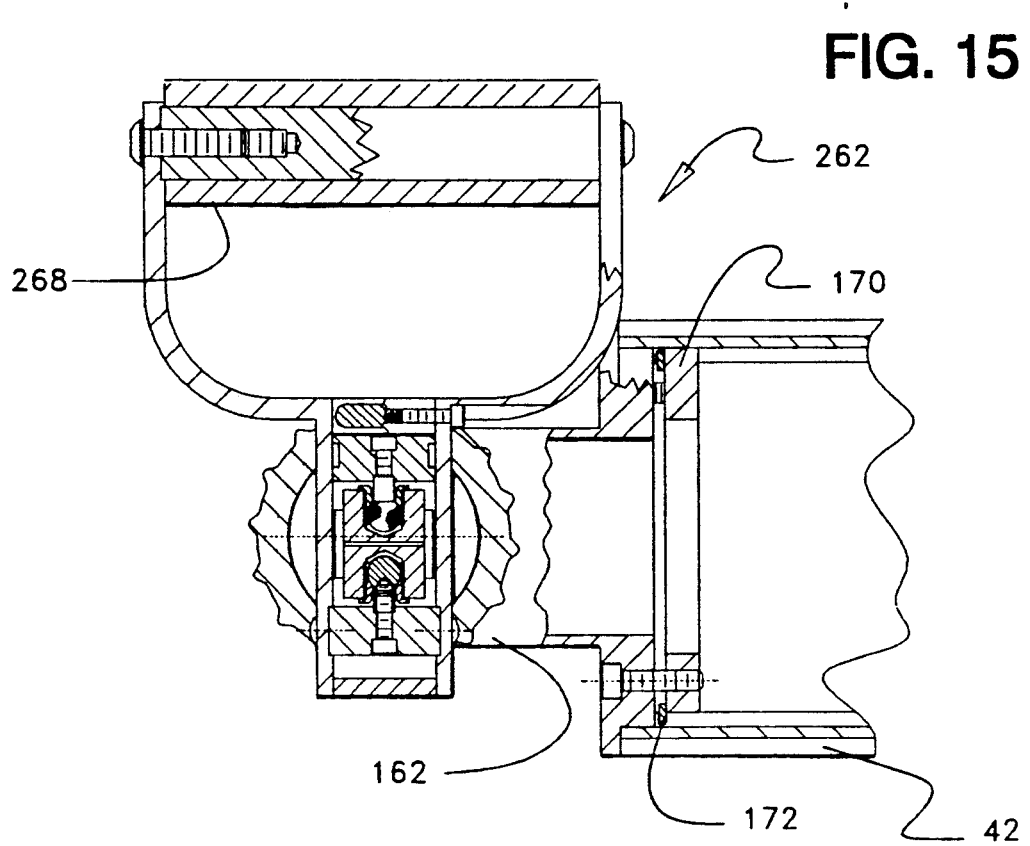
FIG. 15 is a side view of the handle assembly as seen in the direction of arrow 15 of FIG. 14.
Figure 14:
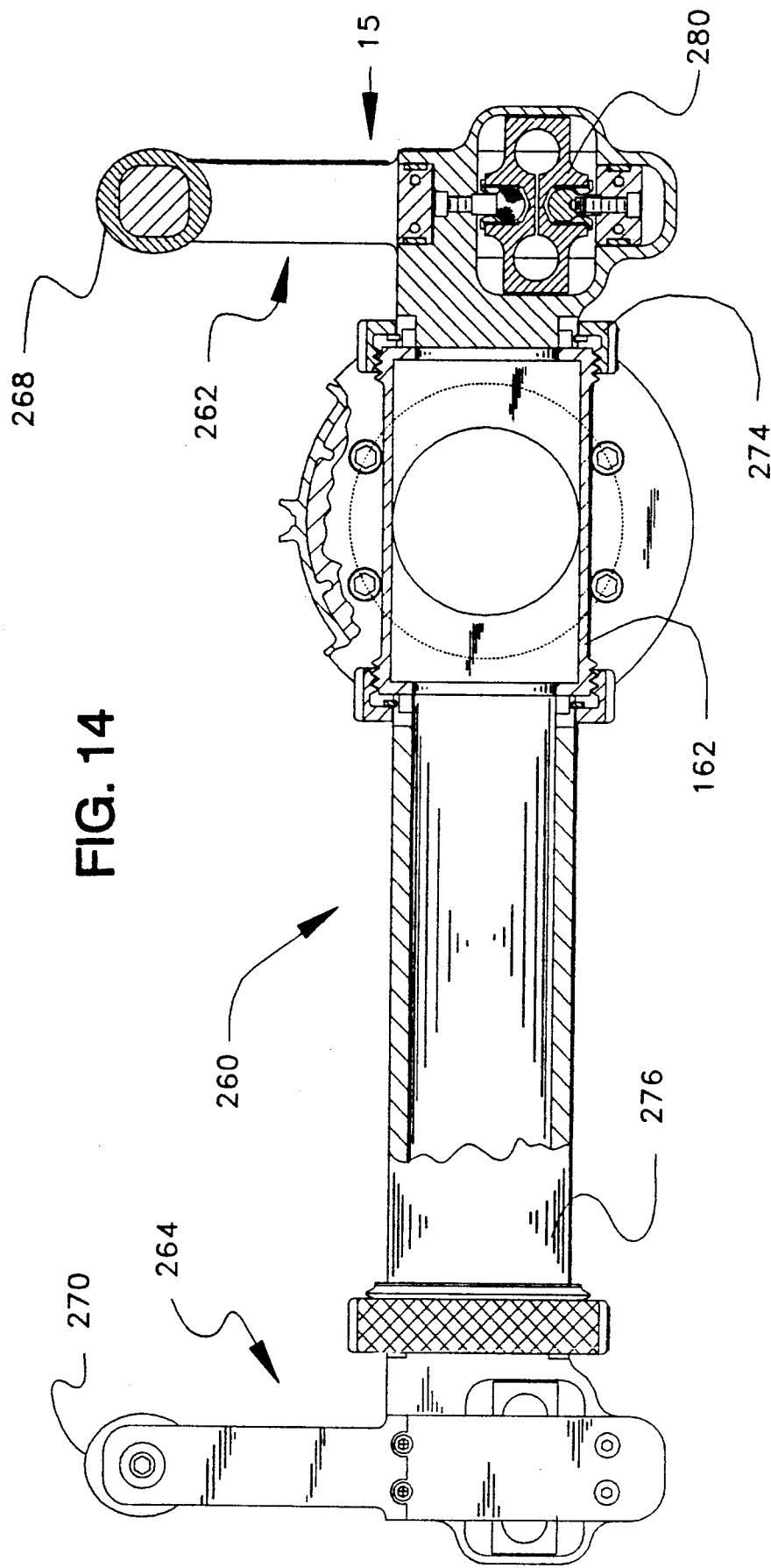
FIG. 14 is an end view, partly broken away and partly in section, of the handle assembly for use in isometric testing.

For isometric testing wherein the endpoint is locked against movement, a handle assembly 260 illustrated in FIGS. 14 and 15 is secured to the end of arm 42 by means of a trunion 162 similar to the one described above in connection with FIGS. 11 and 12. A pair of handle assemblies 262, 264 are detachably secured to trunion 162. The grips 268, 270 of the handle assemblies must be spaced apart at a distance appropriate to meet established test protocols. In this regard, handle assembly 262 is attached directly to trunion 162 by means a threaded retaining means 274, creating a spacing between the centerline of arm 42 and grip 268 of approximately 3½ inches. Handle assembly 264 is attached to trunion 162 via a spacer member 276, creating a spacing between the centerline of arm 42 and grip 270 of 9 inches. In actual operation, the handle assemblies would be connected in a manner that would equally space them from arm 42, thus, FIG. 14 is not representative of an actual handle configuration for testing, but serves the purpose of illustrating handle attachment both with and without spacers. In actual use, without spacers, the grips are spaced 7 inches apart. With the use of two spacers 276, the grips are spaced 18 inches apart. As shown in detail in FIG. 14, handle assembly 262 includes a strain gauge assembly 280, similar to the load cell shown in FIG. 11 for measuring push/pull forces at that handle. Handle assembly 264 includes a similar strain gauge 281 (not shown in FIG. 14). These two strain gauges also permit the measurement of handedness during isometric testing, i.e. a measurement of the proportionate amount of force applied by each hand.

Figure 16:
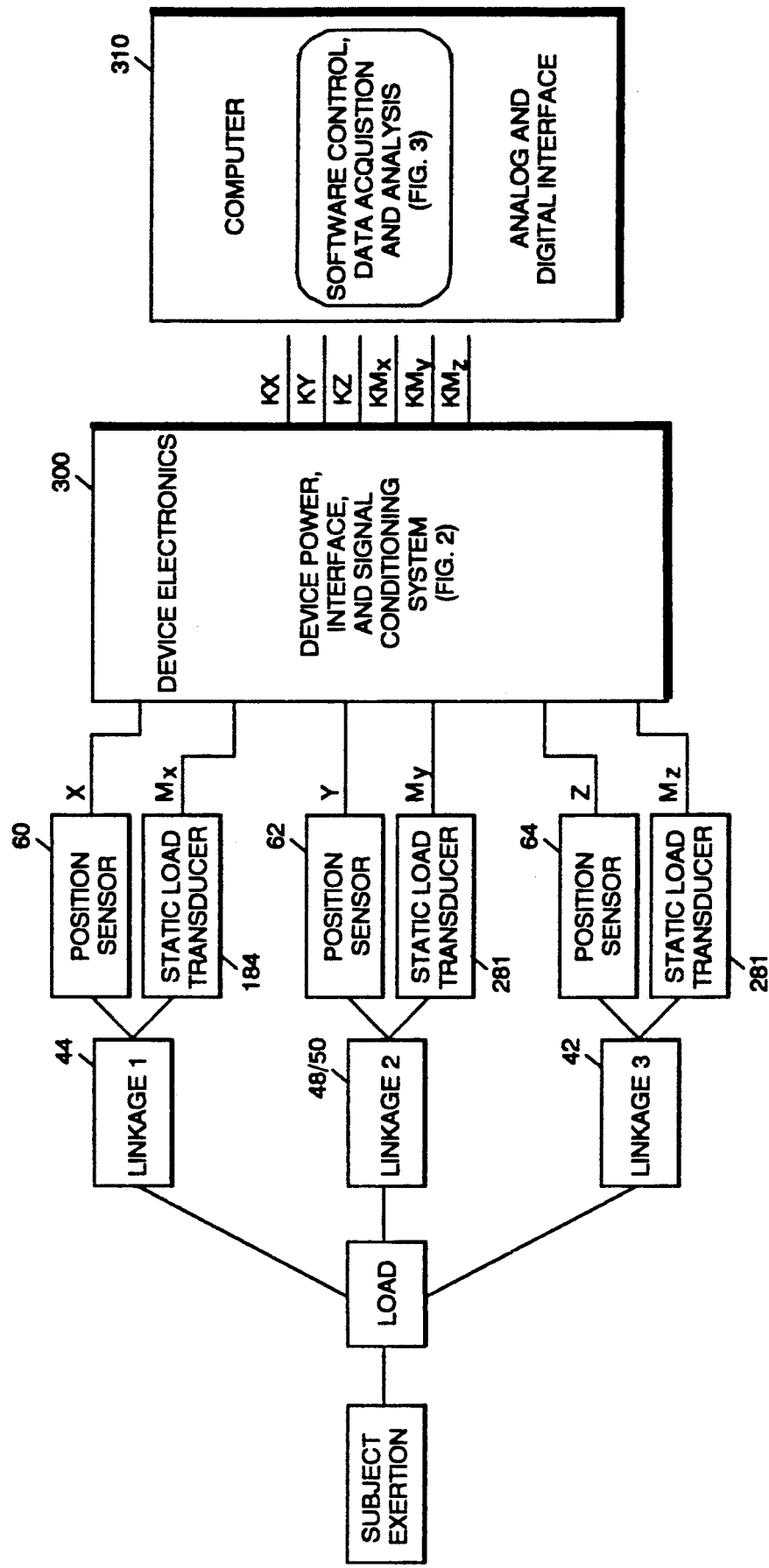
FIG. 16 is an overview diagram of the apparatus and method of the invention as utilized for dynamic and isometric testing.
Figure 17:
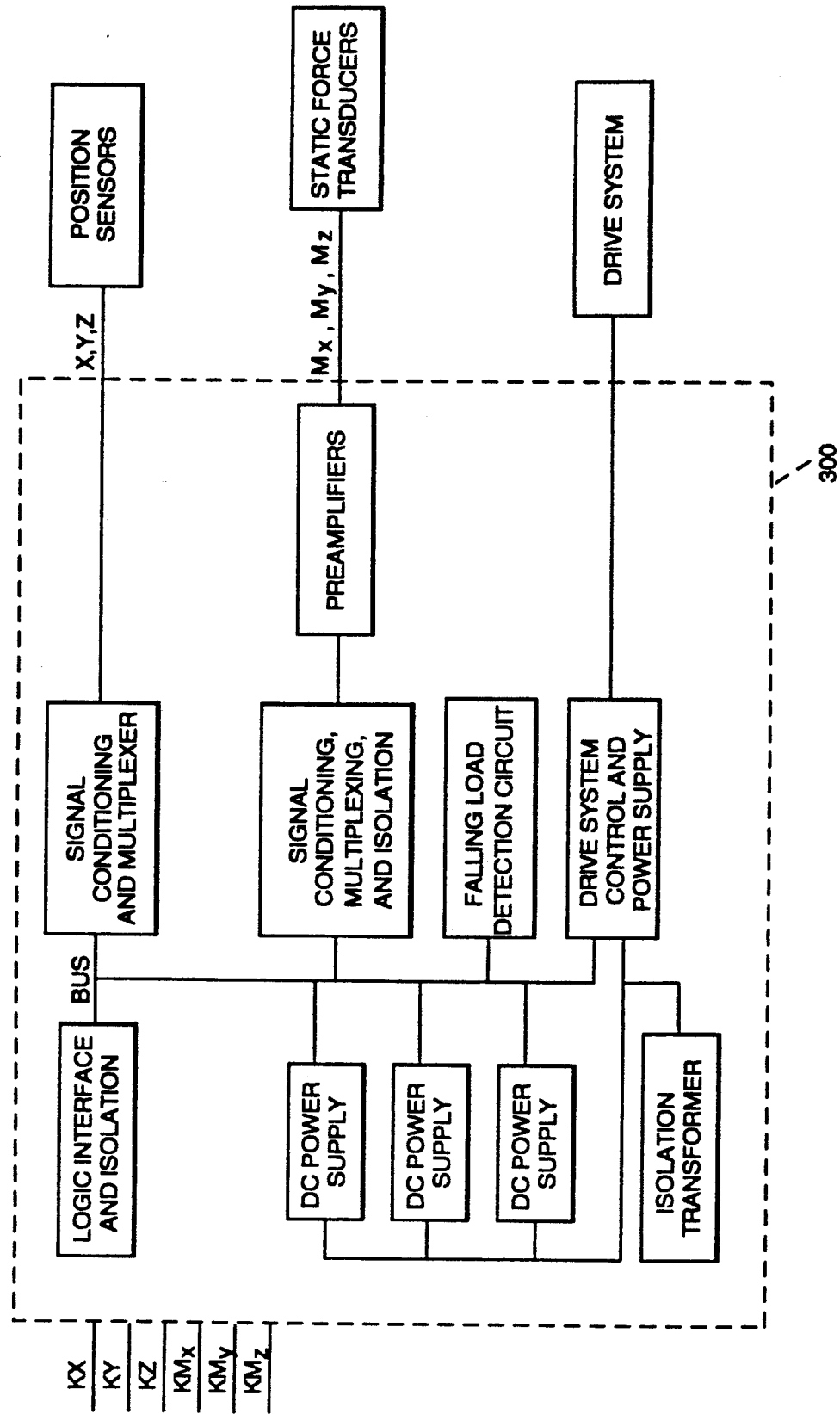
FIG. 17 is a block diagram of the device electronics.

The data processing will now be described with reference to FIGS. 16-18. FIG. 16 is an overall diagram of apparatus 20, including the related computer control as utilized for both dynamic and full isometric operations. As discussed above, in the dynamic mode the subject's exertion on the load provides relative movement of links 44, 48/50 and 42 within the linkage of the cylindrical robot 22. Position sensors 60, 62, 64 produce position signals x, y, z during dynamic testing. Static load transducers 184, 280, 281 produce force signals Mx, My, Mz during isometric testing. All of the above mentioned signals are input to the device electronics 300 which, as shown in more detail in FIG. 17 includes device power means, interface means and a signal conditioning system for producing information KX, KY, KZ and KMx, KMy, KMz input to computer 310. The device electronics 300 also includes means for detecting a falling load which occurs when the test subject has lost control of the load. This means may be rendered operative, for example, by detection of a downward acceleration value above a threshold value for a specified period of time or, in the alternative, may be rendered operative by detection circuitry sensing the test subject's loss of grip with the load at either hand through contact switches (not shown) located where the subject manually engages the load.

Drive electronics 300 further includes the control circuitry for the drive system and associated power supply.

Figure 18:
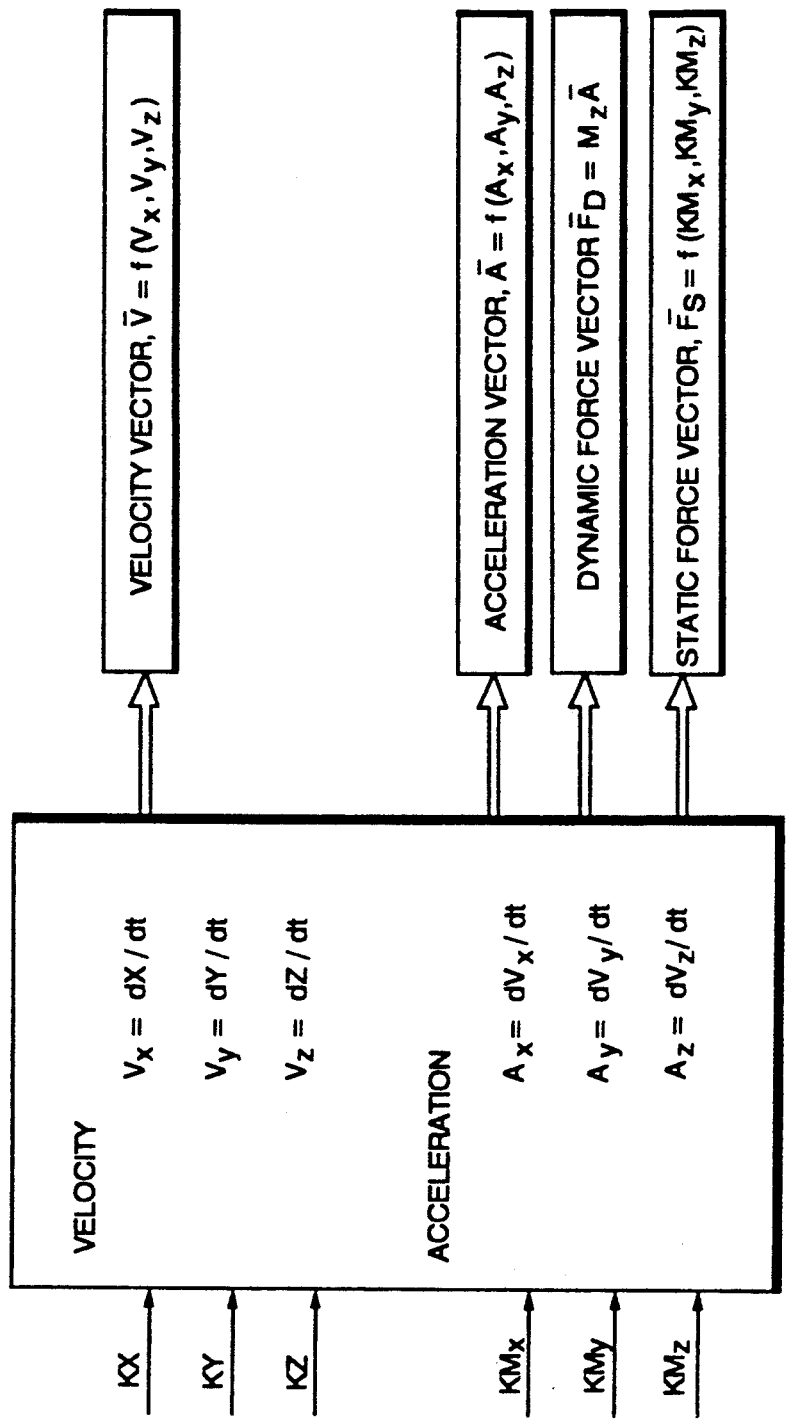
FIG. 18 is a block diagram of the numerical analysis system.

Computer 300 provides an analog and digital interface and also provides the software control and data acquisition and analysis as depicted in more detail in FIG. 18. In this regard, computer 310 preferably handles all force, velocity, acceleration and position information in a cartesian coordinate system. As illustrated, velocity values are computed as, for example, $Vx=dX/dt$ and acceleration values are computed as, for example, $Ax=dVx/dt$, permitting the ultimate computation of the following vectors:
Velocity Vector;
Acceleration Vector;
Dynamic Force Vector; and
Static Force Vector.

The above system described in connection with FIGS. 16-18 permits the input of data from the position sensors and static force transducers and achieves the various processing functions necessary to operate the drive system and falling load safety brake mechanism, while also performing the numerical analysis necessary to control and provide test results in association with the test protocols described in more detail below.

Protocols

In the use of apparatus 20, a preferred isometric protocol consists of seven different tests. Each test positions the individual in a different posture, which is defined by the vertical position of the hands from the center of the two handles, the horizontal position of the feet from the center of the two handles, and the orientation of the arms, legs, and trunk. Table 1 describes the seven standard isometric tests in terms of the anatomical position. The isometric handle attachment for apparatus 20 can vary in width. The width is set to 18 inches for all tests except the leg lift, where it is set to 7 inches. It is critical that the defined position is maintained during the entire isometric effort. For each test, the subject is asked to exert an effort in a particular direction while gripping the handles. All instructions to the subject are objective and given without any emotional appeals. The subject is asked to begin the exertion in a gradual, steady fashion, slowly building up to a maximal effort within the first two seconds. The subject will sustain the maximum exertion for three seconds.

Each test consists of three, five-second trials with a minimum rest period of 30 seconds between each trial. The average force generated during the last three seconds is reported and used to calculate the coefficient of variation (COV) over the three trials. Any of the three trials can be repeated and a new COV is calculated. Only tests with a COV less than or equal to 15% is to be accepted for further analysis. From these tests, the percentile rankings, based on the above mentioned NIOSH industrial norms, are calculated and presented. Also, the Occasional, Frequent and Continuous lifting recommendations for each position are reported as previously described. Two of the static tests involve pushing and pulling postures. NIOSH did not include these static positions in the guidelines, but Blankenship gives percentile rankings, as well as Occasional, Frequent, and Continuous percentages for static pushing and pulling tasks. Blankenship's values are used for these two tests. The seven tests are described below in terms of the anatomical position.

| Test | Horizontal Posture | Vertical Distance |
|---|---|---|
| Arm Lift | Elbows flexed 90 degrees; remaining posture is neutral. | Forearm and length | Elbow height |
| Torso Lift | Hips and shoulders flexed as required by the horizontal and vertical distances; remaining posture is neutral. | 15 in. | 15 in. |
| Leg Lift | Knees, hips, and shoulders flexed as required by the horizontal and vertical distances keeping the trunk as vertical as possible; elbows are neutral | 0 in. | 15 in. |
| High Far Lift | Shoulders and elbows flexed as required by the horizontal and vertical distances; remaining posture is neutral. | 20 in. | 60 in. |
| High Near Lift | Shoulders and elbows flexed as required by the horizontal and vertical distances; remaining posture is neutral. | 10 in. | 60 in. |
| Push | Posture not controlled; amount of trunk inclination | Determined Elbow by posture height | |

-continued

| Test | Horizontal Posture | Vertical Distance |
|---|---|---|
| | suitable to subject; feet staggered. | |
| Pull | Posture not controlled amount of trunk inclination suitable to subject; feet staggered | Determined Elbow height |

As discussed above, the isometric handle attached to apparatus 20 can vary in width. The width will be set to 18 inches for all tests except the Leg Lift where it will be 7 inches. The following percentages reported by Blankenship are used to make the dynamic lifting recommendation.

| Test | Occasional | Frequent | Continuous |
|---|---|---|---|
| Arm Lift | 75% | 40% | 20% |
| Torso Lift | 50% | 40% | 20% |
| Leg Lift | 50% | 40% | 20% |
| High Far | 60% | 40% | 20% |
| High Near | 60% | 40% | 20% |
| Push | 80% | 40% | 20% |
| Pull | 70% | 40% | 20% |

These percentages use the specific extrapolations given for the Occasional lift and the lower end of the range extrapolations given for the Frequent and Continuous lifts. The lower end of the ranges is more consistent with the D.O.T. Physical Demand levels.

The Comprehensive protocol has three phases: an Isometric, a Standard Dynamic, and a Job Task phase. The Isometric phase consists of two of the seven tests from the Isometric protocol: the Arm Lift and the Leg Lift. The testing procedure for the isometric phase of the Comprehensive protocol is identical to the Isometric protocol procedure. Instead of making lifting recommendations directly from the results of the isometric tests, the average forces measured statically helps determine the maximum amount of weight a person can lift dynamically.

The Standard Dynamic phase consists of two sagittal plane lifts and one 3D lift. The sagittal lifts are based on the isometric positions, permitting extrapolations of the isometric results to the dynamic tests.

The first dynamic test is a floor (15 in.) to standard bench height (30 in.) lift. The beginning weight is 40% of the isometric Leg Lift results. The second 2D lift, a waist to shoulder height lift, uses heights normalized to the individual's height rather than standard heights. For this lift, the box is placed on a table adjusted to waist height and positioned under the shelf, which is adjusted to the subject's shoulder. The initial weight for this lift is equal to 80% of the average force produced during the isometric Arm Lift. Using both fixed heights and normalized heights allows for more flexibility in the database. Also, using both heights is necessary in order to extrapolate the beginning loads from the isometric tests, since extrapolations can only be made from the same posture.

To find the maximum weight the person can lift, the protocol uses a modified version of the psychophysical lifting method similar to the one used by Jiang et al. (1986). For each test, a series of five repetition trials are performed. After each trial, the weight is increased by either 2.5, 5, or 10 pound increments, depending on the perceived difficulty of the lifts. This process continues until either the subject wishes to stop or the tester feels it is unsafe for the test to continue, based on observations of the subject. The last weight successfully lifted for all five repetitions is recorded as the maximum weight achieved.

The 3D dynamic test is administered in the same manner as the 2D lifts. The test begins with the box on the floor. The subject picks up the box, turns to the right 90 degrees, takes two to three steps, turns to the left 90 degrees, and places the box on the shelf at bench height. This activity reflects the most frequently occurring lifts observed in industry (Drury et al., 1982, U.S. Department of Labor, 1982). The initial weight used for this lift is 75% of the maximum floor to bench weight measured in the 2D standard dynamic lift. Seventy-five percent was chosen as a safety precaution to compensate for the twisting motions involved during this activity. For these three dynamic lifts, the lifting recommendations are reported on a frequency basis. The Occasional recommendation is the actual maximum lift performed. The Frequent recommendation is 40% of the maximum weight recorded, and the Continuous recommendation is 20% of the maximum weight recorded. These percentages are in agreement with the D.O.T. Physical Demand levels.

The last part of the Comprehensive protocol is the Job Task phase. This phase allows apparatus 20 to be fully utilized in recreating job tasks because the tests are customized, they are not compared in the standard database. To define a task, the tester enters the following:

beginning and ending position of the box (this can be recorded prior to testing by moving the box through one repetition of the task);

number of repetitions performed;

starting weight in box or weight of object if an attachable object is used (weight in box can be expressed as a percentage of an isometric or dynamic result from the first two parts of the protocol, or a specific weight);

any shelf or table heights used.

The maximum weight for each test is found in the same manner as in dynamic testing. Once the maximum weight is found, the MPL and AL can be calculated to determine if the job is acceptable according to the NIOSH guidelines.

In summary, the lifting capability testing apparatus 20 has the capability to measure both isometric and three-dimensional dynamic activities. The related software implements both testing modes with the Isometric and the Comprehensive protocols. The results provide recommendations concerning an individual's lifting capabilities that are based on existing research and databases.

In the drawings and specification there have been disclosed typical preferred embodiments and although specific terms are employed, they are used in a generic and descriptive sense only and not for purposes of limitation, the scope of the invention being set forth in the following claims.

That which we claim is:

1. An apparatus for use in assessing the lifting capability of a human subject, said apparatus providing a dynamic job task phase recreating three-dimensional lifting tasks encountered in actual manual material handling jobs wherein the subject lifts actual job loads such as boxes, bags, asymmetric loads, or the like, and experiences the true weight and inertial effects of the loads, said apparatus comprising:

a device having a rigid, lightweight movable linkage that provides low friction movement between the links thereof, said linkage defining an endpoint having three-dimensional freedom of movement;

means proximate sand endpoint for attaching an actual job load and permitting a test subject to manually engage and lift the actual job load in essentially the same fashion as it would be engaged and lifted in carrying out an actual job lifting task on that load;

means for sensing relative movements within said linkage during lifting of the actual job load and generating signals representative of the position of the endpoint;

said device being fee of load weight simulation and load inertia simulation effects during operation, thereby rendering said device passive during dynamic three-dimensional job task lifting operations performed by the subject; and said movable linkage comprising a cylindrical robot defining an upright column and a horizontal arm mounted for vertical movement along said column, rotatable movement about the axis of said column and linear extension, and a counterbalance assembly for providing a counterbalance to the weight of said arm and any associated mass that travels therewith on said column, said counterbalance assembly comprising a spring member located within said column, a cable secured to said spring member, a grooved spiral cam for taking up said cable and transferring a constant torque to a shaft on which the spiral cam is mounted and means connected to said shaft for transforming said constant torque to a constant linear force and applying the force to the linkage to counterbalance the weight of the linkage.

2. An apparatus for use in assessing the lifting capability of a human subject, said apparatus providing a dynamic job task phase recreating three-dimensional lifting tasks encountered in actual manual material handling jobs wherein the subject lifts actual job loads such as boxes, bags, asymmetric loads, or the like, and experiences the true weight and inertial effects of the loads, said apparatus comprising:

a device having a rigid, lightweight movable linkage that provides low friction movement between the links thereof, said linkage defining an endpoint having three-dimensional freedom of movement;

means proximate said endpoint for attaching an actual job load and permitting a test subject to manually engage and lift the actual job load in essentially the same fashion as it would be engaged and lifted in carrying out an actual job lifting task on that load;

means for sensing relative movements within said linkage during lifting of the actual job load and generating signals representative of the position of the endpoint;

said device being fee of load weight simulation and load inertia simulation effects during operation, thereby rendering said device passive during dynamic three-dimensional job task lifting operations performed by the subject; and said linkage including three links movable along or about three axes and said apparatus further including means for selectively locking a selected number of said links against movement, whereby locking of one link permits movement of said endpoint in a plane, locking of two links permits movement of said endpoint in a line and locking of all three links permits isometric testing at said endpoint.

3. An apparatus as claimed in claim 2 including a counterbalance assembly secured to said linkage for providing a counterbalance to the weight of said linkage during lifting of the load.

4. An apparatus as claimed in claim 2 wherein said device having a movable linkage comprises a cylindrical robot defining an upright column and a horizontal arm mounted for vertical movement along said column, rotatable movement about the axis of said column and linear extension.

5. An apparatus as claimed in claim 2 wherein said device having a movable linkage comprises an elbow arm structure.

6. An apparatus as claimed in claim 2 wherein said device having a movable linkage comprises a gantry structure.

7. An apparatus as claimed in claim 2 including at least one static load transducer for measuring an applied force in an isometric testing mode.

8. An apparatus as claimed in claim 7 including at least one adjustable shelf structure serving as a beginning or terminating location for a three-dimensional lifting task.

9. An apparatus as claimed in claim 2 including a safety brake assembly for engaging and locking said endpoint and attached load against dropping upon sensing the test subject's loss of control of the load.

10. An apparatus as claimed in claim 2 wherein said apparatus is mounted on a platform on which the subject stands during lifting operations, thereby defining a closed-force system.

11. An apparatus for use in assessing the lifting capability of a human subject, said apparatus providing a dynamic job task phase recreating three-dimensional lifting tasks encountered in actual manual material handling jobs wherein the subject lifts actual job loads such as boxes, bags, asymmetric loads, or the like, and experiences the true weight and inertial effects of the loads, said apparatus comprising:

a device having a rigid, lightweight movable linkage that provides low friction movement between the links thereof, said linkage defining an endpoint having three-dimensional freedom of movement;

means proximate said endpoint for attaching an actual job load and permitting a test subject to manually engage and lift the actual job load in essentially the same fashion as it would be engaged and lifted in carrying out an actual job lifting task on that load;

means for sensing relative movements within said linkage during lifting of the actual job load and generating signals representative of the position of the endpoint;

said device being free of load weight simulation and load inertia simulation effects during operation, thereby rendering said device passive during dynamic three-dimensional job task lifting operations performed by the subject; and said movable linkage comprising a cylindrical robot defining an upright column and a horizontal arm mounted for vertical movement along said column and linear extension, and said apparatus further including a drive assembly for raising and lowering said arm on said column, said drive assembly including a directional motor, two paired cable spools driven by said motor and a recirculating cable mounted on said spools and connected to said linkage.

12. An apparatus for use in assessing the lifting capability of a human subject, said apparatus the capability of providing (i) a dynamic job task phase recreating three-dimensional lifting tasks encountered in actual manual material handling jobs wherein the subject lifts actual job loads such as boxes, bags, asymmetric loads, or the like, and experience the true weight and inertial effects of the loads, (ii) a standard dynamic protocol phase consisting of a selected number of two-dimensional and/or three-dimensional lift tests and (iii) an isometric protocol phase including a selected number of static tests, said apparatus comprising:

a cylindrical robot including an upright column, a substantially horizontal arm mounted for vertical movement along said column, rotatable movement about the axis of said column and linear extension, the end of said arm defining an endpoint having three-dimensional freedom of movement within an arcuate region;

means proximate said endpoint for attaching an actual weight to be lifted, including means for attaching an actual job load and permitting a test subject to manually engage the actual job load in the same fashion as it would be engaged in carrying out an actual job task on that load;

a counterbalance assembly secured to said arm for providing a counterbalance to the weight of said arm and any associated mass that travels therewith on said column;

a first position sensor for sensing the vertical location of said arm on said upright column;

a second position sensor for sensing the rotational orientation of said arm with respect to said upright column;

a third position sensor for sensing the degree of linear extension of said arm;

said three position sensors operative in response to the movement of said endpoint to generate signals representative of the position of the endpoint;

means for selectively locking the vertical movement of said arm on said column;

means for selectively locking the rotational movement of said arm with respect to said column;

means for selectively locking the linear extension and retraction movement of said arm;

said cylindrical robot being passive during dynamic lifting operations performed by the subject.

13. An apparatus as claimed in claim 12 including means for sensing sudden downward movement of said endpoint indicative of the test subject's loss of control of the load and a safety brake assembly operative in response to said means for sensing sudden downward movement to lock the endpoint and attached load against dropping.

14. A method for use in assessing the lifting capability of a human subject, said method providing a dynamic job task phase faithfully recreating three-dimensional lifting tasks encountered in actual manual material handling jobs wherein the subject lifts actual job loads such as boxes, bags, asymmetric loads, or the like, and experiences the true weight and inertial effects of the loads, said method comprising:

providing a device having a lightweight, low friction linkage defining an endpoint with three-dimensional freedom of movement;

attaching an actual job load proximate said end point;

selecting a beginning location and a terminating location for the actual job load in a three-dimensional test;

positioning the actual job load at the beginning location;

gripping the actual job load in essentially the same fashion as it would be engaged in carrying out an actual job lifting task on the load, and lifting and moving said actual job load from the beginning location to the terminating location along a path selected by the subject;

during the subject's lifting and movement of the actual job load, permitting the subject to experience the true weight and inertial effects of the load by operating the device having a movable linkage in a passive mode that is free of load weight simulation and load inertia simulation;

sensing the relative movements within the linkage during the subject's lifting and movement of the actual job load and generating signals representative of the position of the endpoint; and processing the data provided by the generated signals to provide a lifting task profile for the test.

15. A method as claimed in claim 14 wherein the step of processing the data includes the step of utilizing a computer (i) to calculate velocity, acceleration and force vectors and (ii) to generate a test result profile based upon the vector values.

16. A method as claimed in claim 14 including the steps of:
   (a) carrying out the subject's lifting and moving of the actual job load in several repetitions to define a job task test phase;
   (b) carrying out a plurality of standard dynamic lifts to define a standard dynamic test phase; and
   (c) locking the linkage to provide a fixed end point and carrying out a plurality of tests by the subject's hand engagement to the end point to define an isometric test phase;
   the job task test phase, standard dynamic test phase and isometric test phase serving to define a comprehensive protocol.

17. A method as claimed in claim 14 including the step, performed prior to the subject's lifting and movement of the actual job load, of entering into a computer information representative of (i) the beginning and ending positions of the actual job load, (ii) the number of repetitions to be performed, (iii) the weight of the actual job load expressed as actual weight or as a percentage of a weight measured in an isometric or dynamic test and (iv) the height of any shelves or tables incorporated into the lifting and moving task.

18. An apparatus for use in assessing the lifting capability of a human subject, said apparatus providing a dynamic job task phase recreating three-dimensional lifting tasks encountered in actual manual material handling jobs wherein the subject lifts actual job loads such as boxes, bags, asymmetric loads, or the like, and experiences the true weight and inertial effects of the loads, said apparatus comprising:

a device having a rigid, lightweight movable linkage that provides low friction movement between the links thereof, said linkage defining an endpoint having three-dimensional freedom of movement;

means proximate said endpoint for attaching an actual job load and permitting a test subject to manually engage and lift the actual job load in essentially the same fashion as it would be engaged and lifted in carrying out an actual job lifting task on that load;

means for sensing relative movements within said linkage during lifting of the actual job load and generating signals representative of the position of the endpoint;

said device being free of load weight simulation and load inertia simulation effects during operation, thereby rendering said device passive during dynamic three-dimensional job task lifting operations performed by the subject; and means for selectively locking the links of said linkage against relative movement to place the apparatus in an isometric mode with a fixed end point, and an associated handle assembly secured to the linkage at the end point, said handle assembly comprising a grip for each hand, means for measuring push/pull forces, and means for measuring handedness by measuring the proportionate amount of force applied by each hand.

* * * * *